US005849549A

United States Patent [19]

Barnett et al.

[11] Patent Number: 5,849,549

[45] Date of Patent: Dec. 15, 1998

[54] OXIDATIVELY STABLE ALPHA-AMYLASE

[75] Inventors: Christopher C. Barnett, South San Francisco, Calif.; Leif P. Solheim, Clinton, Iowa; Colin Mitchinson, Half Moon Bay, Calif.; Scott D. Power, San Bruno, Calif.; Carol A. Requadt, Tiburon, Calif.

[73] Assignee: Genencor International, Palo Alto, Calif.

[21] Appl. No.: 468,698

[22] Filed: Jun. 6, 1995

Related U.S. Application Data

[60] Division of Ser. No. 194,664, Feb. 10, 1994, which is a continuation-in-part of Ser. No. 16,395, Feb. 11, 1993, abandoned.

[51] Int. Cl.[6] .............................. C12P 19/14; C12N 9/28; C12N 15/56; C12N 15/09

[52] U.S. Cl. ......................... 435/99; 435/202; 435/172.1; 435/172.3; 935/10; 536/23.2

[58] Field of Search .......................... 435/99, 202, 172.1, 435/172.3; 935/10; 536/23.2

[56] References Cited

U.S. PATENT DOCUMENTS

| | | | |
|---|---|---|---|
| 4,261,868 | 4/1981 | Hora et al. | 252/529 |
| 4,284,722 | 8/1981 | Tamuri et al. | 435/94 |
| 4,493,893 | 1/1985 | Mielenz, et al. | 435/172.3 |
| 4,620,936 | 11/1986 | Kielman et al. | 252/99 |
| 4,634,551 | 1/1987 | Burns et al. | 252/102 |
| 4,732,973 | 3/1988 | Barr et al. | 530/350 |
| 4,752,585 | 6/1988 | Koths et al. | 435/256 |
| 4,760,025 | 7/1988 | Estell et al. | 435/256 |
| 4,863,626 | 9/1989 | Coyne et al. | 252/91 |
| 5,118,623 | 6/1992 | Boguslawski et al. | 435/222 |
| 5,322,778 | 6/1994 | Antrim et al. | 435/99 |
| 5,346,823 | 9/1994 | Estell et al. | 435/222 |

FOREIGN PATENT DOCUMENTS

| | | |
|---|---|---|
| 0 130 756 | 1/1985 | European Pat. Off. . |
| 0 285 123 | 5/1988 | European Pat. Off. . |
| 0 409 299 | 1/1991 | European Pat. Off. . |
| 0 410 498 | 1/1991 | European Pat. Off. . |
| 0 676 456 | 11/1992 | France . |
| 91/00353 | 1/1991 | WIPO . |
| 91/16423 | 10/1991 | WIPO . |
| 92/08778 | 5/1992 | WIPO . |
| 94/02597 | 2/1994 | WIPO . |

OTHER PUBLICATIONS

Bealinkelly et al, "Studies on the thermostability of the alpha–amylase of *bacillus–caldovelox*" Appl. Microbiol. and Biotech 36(3):332–336 (Dec. 1991).

Brosnan, et al., "Investigation of the mechanism of irreversible thermoinactivation of *bacillus–stearothermophilus* alpha–amylase" Eur. J. of Biochem. 203(1–2)225–231 (Jan. 1992).

Declerck, et al., "Use of Amber Suppressors to Investigate the Thermostability of *Bacillus licheniformis* α–Amylase" J. of Biol. Chem. 265(26):15481–15488 (1990).

Estell, et al., "Engineering an enzyme by Site–directed Mutagenesis to Be Resistant to Chemical Oxidation" J. of Biol. Chem. 260(11)6518–6521 (Jun. 1985).

(List continued on next page.)

*Primary Examiner*—Rebecca E. Prouty
*Attorney, Agent, or Firm*—Christopher L. Stone

[57] ABSTRACT

Novel alpha-amylase mutants derived from the DNA sequences of naturally occurring or recombinant alpha-amylases are disclosed. The mutant alpha-amylases, in general, are obtained by in vitro modifications of a precursor DNA sequence encoding the naturally occurring or recombinant alpha-amylase to generate the substitution (replacement) or deletion of one or more oxidizable amino acid residues in the amino acid sequence of a precursor alpha-amylase. Such mutant alpha-amylases have altered oxidative stability and/or altered pH performance profiles and/or altered thermal stability as compared to the precursor. Also disclosed are detergent and starch liquefaction compositions comprising the mutant amylases, as well as methods of using the mutant amylases.

2 Claims, 22 Drawing Sheets

OTHER PUBLICATIONS

Gray, et al., "Structural Genes Encoding the Thermophilic α–amylases of *Bacillus sterothermophilus* and *Bacillus licheniformis*" J. Bact. 166(2):635–643 (May 1986).

Holm et al., "Random Mutagenesis used to probe the structure and function of *Bacillus stearothermophilus* alpha–amylase" Prot. Engineering 3(3):181–191 (1990).

Janecek, et al., "α–Amylases and approaches leading to their enhanced stability" FEBS 11085 304(1,1–3):1–3 (Jun. 1992).

Jorgenesen, "Cloning of a chromosomal α–amylase gene from *Bacillus stearothermophilus*" FEMS Microbiology Letters 77:271–276 (1991).

Joyet, et al., "Hyperthermostable variants of a highly thermostable alpha–amylase" Biotechnology 10:1579–1583 (Dec. 1992).

Manning, et al., "Thermostable α–Amyulase of *Bacillus stearothermophilus*" J. of Biol. Chem. 236(11):2952–2965 (Nov. 1961).

Matsui, et al., "A mutant α–amylase with enhanced activity specific for short substrates" FEBS 11596 310(3):216–218 (Oct. 1992).

Matsui et al., "An increase in the transglycosylation activity of Saccharomycopsis α–amylase altered by site–directed mutagenesis" Biochimica et Biophysica Acta 1077:416–419 (1991).

Matsuura et al., "Structure and Possible Catalytic Residues of Taka–Amylase A" J. Biochemistry 95:697–702 (1984).

Nakajima, et al., "Nucleotide Sequence of the *Bacillus stearothermophilus* α–Amylase Gene" J. Bacteriology 163(1):401–406 (Jul. 1985).

Ogasahara, et al., "Studies on Thermophilic α–Amylase from *Bacillus stearothemorphilus*" J. Biochem. 67(1):65–89 (1970).

Ottesen et al., "The Subtilisins" Methods in Enzymology 19:199–215 (1970).

Sogaard et al., "Site–directed Mutagenesis of Histidine 93, Aspartic Acid 180, Glutamic Acid 205, Histidine 290, and Aspartic Acid 291 at the Active Site and Tryphtophan 279 at the Raw Starch Binding site in Barley α–Amylase 1" J. Biol. Chem. 268(32) 22480–22484 (Oct. 1993).

Suzuki, et al., "Amino Acid Residues Stabilizing a Bacillus α–Amylase against Irreversible Thermoinactivation" J. Biol. Chem. 264(32):18933–18938 (Nov. 1989).

Svensson, et al., "Mutational analysis of glucosylase function" J. Biotech. 29:1–37 (1993).

Takase et al., "Site–directed mutagenesis of active site residues in *Bacillus subtilis* α–amylase" Biochimica et Biophysica Acta 1120–281–288 (1992).

Tomazic et al., "Mechanisms of irreversible Thermal Inactiviation of Bacillus α–Amylases" J. of Biol. Chem. 262(7):3086–3091 (Mar. 1988).

Vihinen et al. "Site–Directed Mutagenesis of a Thermostable α–Amylase from *Bacillus stearothermophilus*: Punitive Role of Three Conserved Residues" J. Biochem 107:267–272 (1990).

```
          10                                      30                                     50
AGCTTGAAGAAGTGAAGAAGCAGAGAGGCTATTGAATAAATGAGTAGAAAGCGCCATATC

          70                                      90                                    110
GGCGCTTTTCTTTTGGAAGAAAATATAGGGAAAATGGTACTTGTTAAAAATTCGGAATAT

         130                                     150                                    170
TTATACAACATCATATGTTTCACATTGAAAGGGGAGGAGAATCATGAAACAACAAAAACG
                                                    M  K  Q  Q  K  R

         190                                     210                                    230
GCTTTACGCCCGATTGCTGACGCTGTTATTTGCGCTCATCTTCTTGCTGCCTCATTCTGC
 L  Y  A  R  L  L  T  L  L  F  A  L  I  F  L  L  P  H  S  A

         250                                     270                                    290
AGCAGCGGCGGCAAATCTTAATGGGACGCTGATGCAGTATTTTGAATGGTACATGCCCAA
 A  A  A  A  N  L  N  G  T  L  M  Q  Y  F  E  W  Y  M  P  N

         310                                     330                                    350
TGACGGCCAACATTGGAAGCGTTTGCAAAACGACTCGGCATATTTGGCTGAACACGGTAT
 D  G  Q  H  W  K  R  L  Q  N  D  S  A  Y  L  A  E  H  G  I

         370                                     390                                    410
TACTGCCGTCTGGATTCCCCCGGCATATAAGGGAACGAGCCAAGCGGATGTGGGCTACGG
 T  A  V  W  I  P  P  A  Y  K  G  T  S  Q  A  D  V  G  Y  G

         430                                     450                                    470
TGCTTACGACCTTTATGATTTAGGGGAGTTTCATCAAAAAGGGACGGTTCGGACAAAGTA
 A  Y  D  L  Y  D  L  G  E  F  H  Q  K  G  T  V  R  T  K  Y

         490                                     510                                    530
CGGCACAAAAGGAGAGCTGCAATCTGCGATCAAAAGTCTTCATTCCCGCGACATTAACGT
 G  T  K  G  E  L  Q  S  A  I  K  S  L  H  S  R  D  I  N  V

         550                                     570                                    590
TTACGGGGATGTGGTCATCAACCACAAAGGCGGCGCTGATGCGACCGAAGATGTAACCGC
 Y  G  D  V  V  I  N  H  K  G  G  A  D  A  T  E  D  V  T  A

         610                                     630                                    650
GGTTGAAGTCGATCCCGCTGACCGCAACCGCGTAATTTCAGGAGAACACCTAATTAAAGC
 V  E  V  D  P  A  D  R  N  R  V  I  S  G  E  H  L  I  K  A

         670                                     690                                    710
CTGGACACATTTTCATTTTCCGGGGCGCGGCAGCACATACAGCGATTTTAAATGGCATTG
 W  T  H  F  H  F  P  G  R  G  S  T  Y  S  D  F  K  W  H  W

         730                                     750                                    770
GTACCATTTTGACGGAACCGATTGGGACGAGTCCCGAAAGCTGAACCGCATCTATAAGTT
 Y  H  F  D  G  T  D  W  D  E  S  R  K  L  N  R  I  Y  K  F

         790                                     810                                    830
TCAAGGAAAGGCTTGGGATTGGGAAGTTTCCAATGAAAACGGCAACTATGATTATTTGAT
 Q  G  K  A  W  D  W  E  V  S  N  E  N  G  N  Y  D  Y  L  M
```

*FIG._1A*

```
          850                 870                 890
GTATGCCGACATCGATTATGACCATCCTGATGTCGCAGCAGAAATTAAGAGATGGGGCAC
 Y  A  D  I  D  Y  D  H  P  D  V  A  A  E  I  K  R  W  G  T

          910                 930                 950
TTGGTATGCCAATGAACTGCAATTGGACGGTTTCCGTCTTGATGCTGTCAAACACATTAA
 W  Y  A  N  E  L  Q  L  D  G  F  R  L  D  A  V  K  H  I  K

          970                 990                1010
ATTTTCTTTTTTGCGGGATTGGGTTAATCATGTCAGGGAAAAAACGGGGAAGGAAATGTT
 F  S  F  L  R  D  W  V  N  H  V  R  E  K  T  G  K  E  M  F

         1030                1050                1070
TACGGTAGCTGAATATTGGCAGAATGACTTGGGCGCTCTGGAAAACTATTTGAACAAAAC
 T  V  A  E  Y  W  Q  N  D  L  G  A  L  E  N  Y  L  N  K  T

         1090                1110                1130
AAATTTTAATCATTCAGTGTTTGACGTGCCGCTTCATTATCAGTTCCATGCTGCATCGAC
 N  F  N  H  S  V  F  D  V  P  L  H  Y  Q  F  H  A  A  S  T

         1150                1170                1190
ACAGGGAGGCGGCTATGATATGAGGAAATTGCTGAACGGTACGGTCGTTTCCAAGCATCC
 Q  G  G  G  Y  D  M  R  K  L  L  N  G  T  V  V  S  K  H  P

         1210                1230                1250
GTTGAAATCGGTTACATTTGTCGATAACCATGATACACAGCCGGGGCAATCGCTTGAGTC
 L  K  S  V  T  F  V  D  N  H  D  T  Q  P  G  Q  S  L  E  S

         1270                1290                1310
GACTGTCCAAACATGGTTTAAGCCGCTTGCTTACGCTTTTATTCTCACAAGGGAATCTGG
 T  V  Q  T  W  F  K  P  L  A  Y  A  F  I  L  T  R  E  S  G

         1330                1350                1370
ATACCCTCAGGTTTTCTACGGGGATATGTACGGGACGAAAGGAGACTCCCAGCGCGAAAT
 Y  P  Q  V  F  Y  G  D  M  Y  G  T  K  G  D  S  Q  R  E  I

         1390                1410                1430
TCCTGCCTTGAAACACAAAATTGAACCGATCTTAAAACGCAGAAAACAGTATGCGTACGG
 P  A  L  K  H  K  I  E  P  I  L  K  A  R  K  Q  Y  A  Y  G

         1450                1470                1490
AGCACAGCATGATTATTTCGACCACCATGACATTGTCGGCTGGACAAGGGAAGGCGACAG
 A  Q  H  D  Y  F  D  H  H  D  I  V  G  W  T  R  E  G  D  S

         1510                1530                1550
CTCGGTTGCAAATTCAGGTTTGGCGGCATTAATAACAGACGGACCCGGTGGGGCAAAGCG
 S  V  A  N  S  G  L  A  A  L  I  T  D  G  P  G  G  A  K  R

         1570                1590                1610
AATGTATGTCGGCCGGCAAAACGCCGGTGAGACATGGCATGACATTACCGGAAACCGTTC
 M  Y  V  G  R  Q  N  A  G  E  T  W  H  D  I  T  G  N  R  S

         1630                1650                1670
GGAGCCGGTTGTCATCAATTCGGAAGGCTGGGGAGAGTTTCACGTAAACGGCGGGTCGGT
 E  P  V  V  I  N  S  E  G  W  G  E  F  H  V  N  G  G  S  V
```

*FIG._1B*

```
      1690                  1710                  1730
TTCAATTTATGTTCAAAGATAGAAGAGCAGAGAGGACGGATTTCCTGAAGGAAATCCGTT
 S   I   Y   V   Q   R   *

      1750                  1770                  1790
TTTTTATTTTGCCCGTCTTATAAATTTCTTTGATTACATTTTATAATTAATTTTAACAAA

      1810                  1830                  1850
GTGTCATCAGCCCTCAGGAAGGACTTGCTGACAGTTTGAATCGCATAGGTAAGGCGGGGA

      1870                  1890                  1910
TGAAATGGCAACGTTATCTGATGTAGCAAAGAAAGCAAATGTGTCGAAAATGACGGTATC

      1930                  1950
GCGGGTGATCAATCATCCTGAGACTGTGACGGATGAATTGAAAAAGCT
```

FIG._1C

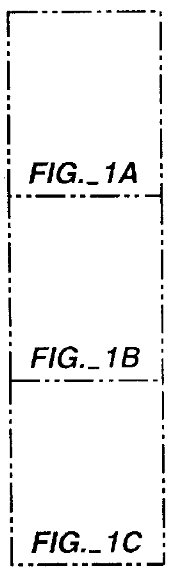

FIG._1

```
        10                                 30                             50
ANLNGTLMQYFEWYMPNDGQHWKRLQNDSAYLAEHGITAVWIPPAYKGTSQADVGYGAYD

        70                                 90                             110
LYDLGEFHQKGTVRTKYGTKGELQSAIKSLHSRDINVYGDVVINHKGGADATEDVTAVEV

        130                                150                            170
DPADRNRVISGEHLIKAWTHFHFPGRGSTYSDFKWHWYHFDGTDWDESRKLNRIYKFQGK

        190                                210                            230
AWDWEVSNENGNYDYLMYADIDYDHPDVAAEIKRWGTWYANELQLDGFRLDAVKHIKFSF

        250                                270                            290
LRDWVNHVREKTGKEMFTVAEYWQNDLGALENYLNKTNFNHSVFDVPLHYQFHAASTQGG

        310                                330                            350
GYDMRKLLNGTVVSKHPLKSVTFVDNHDTQPGQSLESTVQTWFKPLAYAFILTRESGYPQ

        370                                390                            410
VFYGDMYGTKGDSQREIPALKHKIEPILKARKQYAYGAQHDYFDHHDIVGWTREGDSSVA

        430                                450                            470
NSGLAALITDGPGGAKRMYVGRQNAGETWHDITGNRSEPVVINSEGWGEFHVNGGSVSIY

VQR
```

*FIG._2*

Am-Lich = *B.Licheniformis* Am-Amylo = *B.amyloliquefaciens* Am-Stearo = *B.stearothermophilus*

```
                                                                       1           19
           1                                                                       60
Am-Lich    ..............MKQQ KRLYARLLTL LFALIFLLPH ...............SAAA AANLNGTLMQ YFEWYMPNDG
Am-Amylo   MRGRGNMIQK RKRTVSFRLV LMCTLLFVSL .................PITK TSAVNGTLMQ YFEWYTPNDG
Am-Stearo  ................VLTF HRIIRKGWMF LLAFLLTASL FCPTGRHAKA AAPFNGTMMQ YFEWYLPDDG

                                                                                   79
           61                                                                      120
Am-Lich    QHWKRLQNDS AYLAEHGITA VWIPPAYKGT SQADVGYGAY DLYDLGEFHQ KGTVRTKYGT
Am-Amylo   QHWKRLQNDA EHLSDIGITA VWIPPAYKGL SQSDNGYGPY DLYDLGEFQQ KGTVRTKYGT
Am-Stearo  TLWTKVANEA NNLSSLGITA LSLPPAYKGL SRSDVGYGVY DLYDLGEFNQ KGTVRTKYGT

                                                                                   139
           121                                                                     180
Am-Lich    KGELQSAIKS LHSRDINVYG DVVINHKGGA DATEDVTAVE VDPADRNRVI SGEHLIKAWT
Am-Amylo   KSELQDAIGS LHSRNVQVYG DVVLNHKAGA DATEDVTAVE VNPANRNQET SEEYQIKAWT
Am-Stearo  KAQYLQAIQA AHAAGMQVYA DVVFDHKGGA DGTEWVDAVE VNPSDRNQEI SGTYQIQAWT

                                                                                   197
           181                                                                     240
Am-Lich    HFHFPGRGST YSDFKWHWYH FDGTDWDESR KLNRIYKF.... QGKAWDWEVS NENGNYDYLM
Am-Amylo   DFRFPGRGNT YSDFKWHWYH FDGADWDESR KISRIFKFRG EGKAWDWEVS SENGNYDYLM
Am-Stearo  KFDFPGRGNT YSSFKWRWYH FDGVDWDESR KLSRIYKFRG IGKAWDWEVD TENGNYDYLM

                                                                                   257
           241                                                                     300
Am-Lich    YADIDYDHPD VAAEIKRWGT WYANELQLDG FRLDAVKHIK FSFLRDWVNH VREKTGKEMF
Am-Amylo   YADVDYDHPD VVAETKKWGI WYANELSDLG FRIDAAKHIK FSFLRDWVQA VRQATGKEMF
Am-Stearo  YADLDMDHPE VVTELKNWGK WYVNTTNIDG FRLDGLKHIK FSFFPDWLSY VRSQTGKPLF

                                                                                   317
           301                                                                     360
Am-Lich    TVAEYWQNDL GALENYLNKT NFNHSVFDVP LHYQFHAAST QGGGYDMRKL LNGTVVSKHP
Am-Amylo   TVAEYWQNNA GKLENYLNKT SFNQSVFDVP LHFNLQAASS QGGGYDMRRL LDGTVVSRHP
Am-Stearo  TVGEYWSYDI NKLHNYITKT NGTMSLFDAP LHNKFYTASK SGGAFDMRTL MTNTLMKDQP
```

FIG._3A

```
                                                                          377
           361                                                            420
Am-Lich    LKSVTFVDNH DTQPGQSLES TVQTWFKPLA YAFILTRESG YPQVFYGDMY GTKGDSQREI
Am-Amylo   EKAVTFVENH DTQPGQSLES TVQTWFKPLA YAFILTRESG YPQVFYGDMY GTKGTSPKEI
Am-Stearo  TLAVTFVDNH DTNPAKR..CS HGRPWFKPLA YAFILTRQEG YPCVFYGDYY GI.........PQYNI

                                                                          437
           421                                                            480
Am-Lich    PALKHKIEPI LKARKQYAYG AQHDYFDHHD IVGWTREGDS SVANSGLAAL ITDGPGGAKR
Am-Amylo   PSLKDNIEPI LKARKEYAYG PQHDYIDHPD VIGWTREGDS SAAKSGLAAL ITDGPGGSKR
Am-Stearo  PSLKSKIDPL LIARRDYAYG TQHDYLDHSD IIGWTREGVT EKPGSGLAAL ITDGAGRSKW

                                                    483
           481                                                            540
Am-Lich    MYVGRQNAGE TWHDITGNRS EPVVINSEGW GEFHVNGGSV SIYVQR......... ....................
Am-Amylo   MYAGLKNAGE TWYDITGNRS DTVKIGSDGW GEFHVNDGSV SIYVQK......... ....................
Am-Stearo  MYVKGQHAGK VFYDLTGNRS DTVTINSDGW GEFKVNGGSV SVWVPRKTTV STIARPITTR

           541              559
Am-Lich    ........................ .................
Am-Amylo   ........................ .................
Am-Stearo  PWTGEFVRWH EPRLVAWP*
```

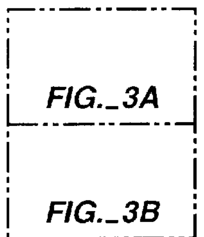

10 30 50
ANLNGTLMQYFEWYMPNDGQHWKRLQNDSAYLAEHGITAVWIPPAYKGTSQADVGYGAYD 70 90 110
LYDLGEFHQKGTVRTKYGTKGELQSAIKSLHSRDINVYGDVVINHKGGADATEDVTAVEV 130 150 170
DPADRNRVISGEHLIKAWTHFHFPGRGSTYSDFKWHWYHFDGTDWDESRKLNRIYKFQGK 190 210 230
AWDWEVSNENGNYDYLTYADIDYDHPDVAAEIKRWGTWYANELQLDGFRLDAVKHIKFSF 250 270 290
LRDWVNHVREKTGKEMFTVAEYWQNDLGALENYLNKTNFNHSVFDVPLHYQFHAASTQGG 310 330 350
GYDMRKLLNGTVVSKHPLKSVTFVDNHDTQPGQSLESTVQTWFKPLAYAFILTRESGYPQ 370 390 410
VFYGDMYGTKGDSQREIPALKHKIEPILKARKQYAYGAQHDYFDHHDIVGWTREGDSSVA 430 450 470
NSGLAALITDGPGGAKRMYVGRQNAGETWHDITGNRSEPVVINSEGWGEFHVNGGSVSIY

VQR

*FIG._4a*

AAAA 14 34 54
ANLNGTLMQYFEWYMPNDGQHWKRLQNDSAYLAEHGITAVWIPPAYKGTSQADVGYGAYD 74 94 114
LYDLGEFHQKGTVRTKYGTKGELQSAIKSLHSRDINVYGDVVINHKGGADATEDVTAVEV 134 154 174
DPADRNRVISGEHLIKAWTHFHFPGRGSTYSDFKWHWYHFDGTDWDESRKLNRIYKFQGK 194 214 234
AWDWEVSNENGNYDYLMYADIDYDHPDVAAEIKRWGTWYANELQLDGFRLDAVKHIKFSF 254 274 294
LRDWVNHVREKTGKEMFTVAEYWQNDLGALENYLNKTNFNHSVFDVPLHYQFHAASTQGG 314 334 354
GYDMRKLLNGTVVSKHPLKSVTFVDNHDTQPGQSLESTVQTWFKPLAYAFILTRESGYPQ 374 394 414
VFYGDMYGTKGDSQREIPALKHKIEPILKARKQYAYGAQHDYFDHHDIVGWTREGDSSVA 434 454 474
NSGLAALITDGPGGAKRMYVGRQNAGETWHDITGNRSEPVVINSEGWGEFHVNGGSVSIY

VQR

*FIG._4b*

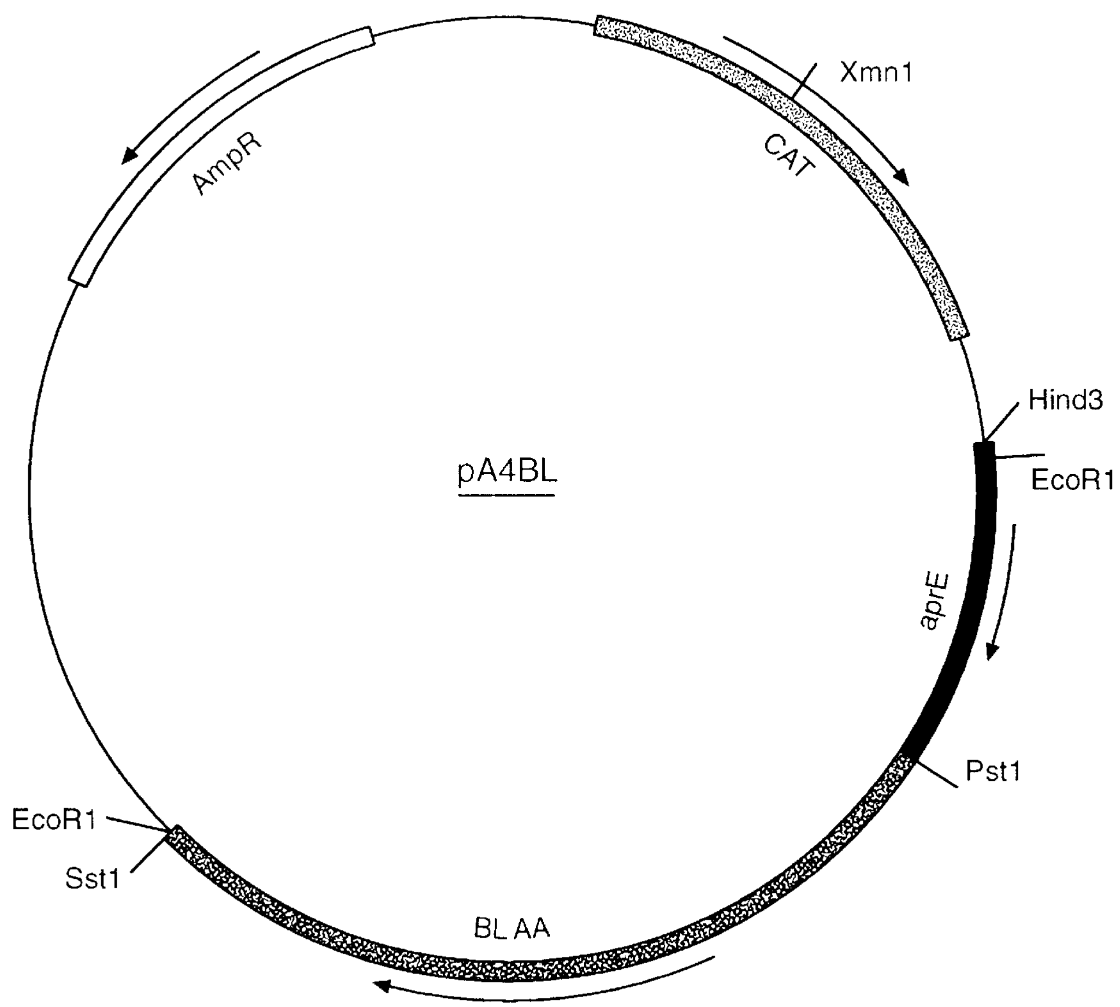
FIG._5

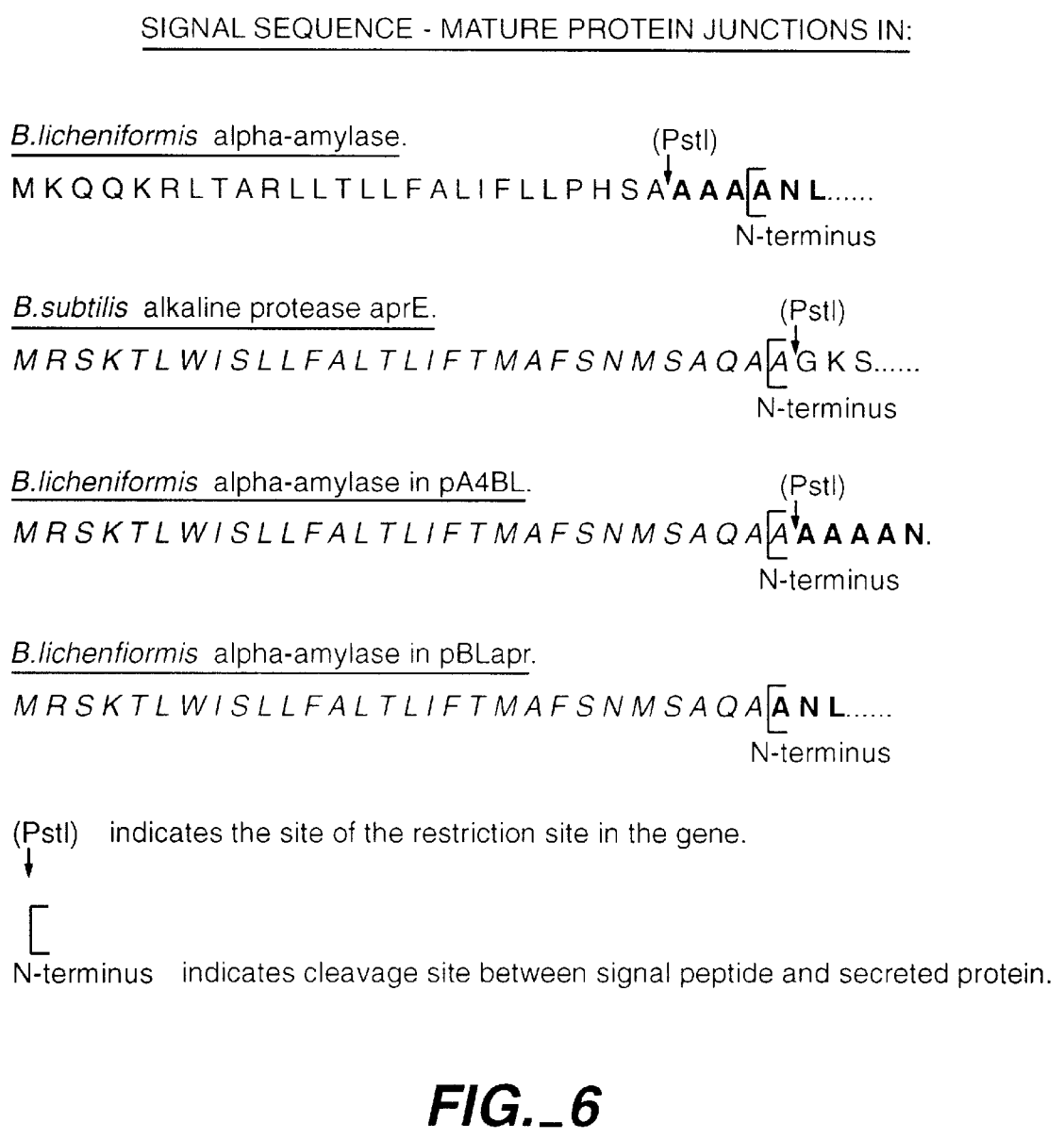

SIGNAL SEQUENCE - MATURE PROTEIN JUNCTIONS IN:

*B.licheniformis* alpha-amylase.

(PstI)

M K Q Q K R L T A R L L T L L F A L I F L L P H S A A A A [A N L......

N-terminus

*B.subtilis* alkaline protease aprE.

(PstI)

*M R S K T L W I S L L F A L T L I F T M A F S N M S A Q A* [*A* G K S......

N-terminus

*B.licheniformis* alpha-amylase in pA4BL.

(PstI)

*M R S K T L W I S L L F A L T L I F T M A F S N M S A Q A* [*A* A A A A N.

N-terminus

*B.lichenfiormis* alpha-amylase in pBLapr.

*M R S K T L W I S L L F A L T L I F T M A F S N M S A Q A* [A N L......

N-terminus (PstI) ↓ indicates the site of the restriction site in the gene.

[ N-terminus indicates cleavage site between signal peptide and secreted protein.

*FIG._6*

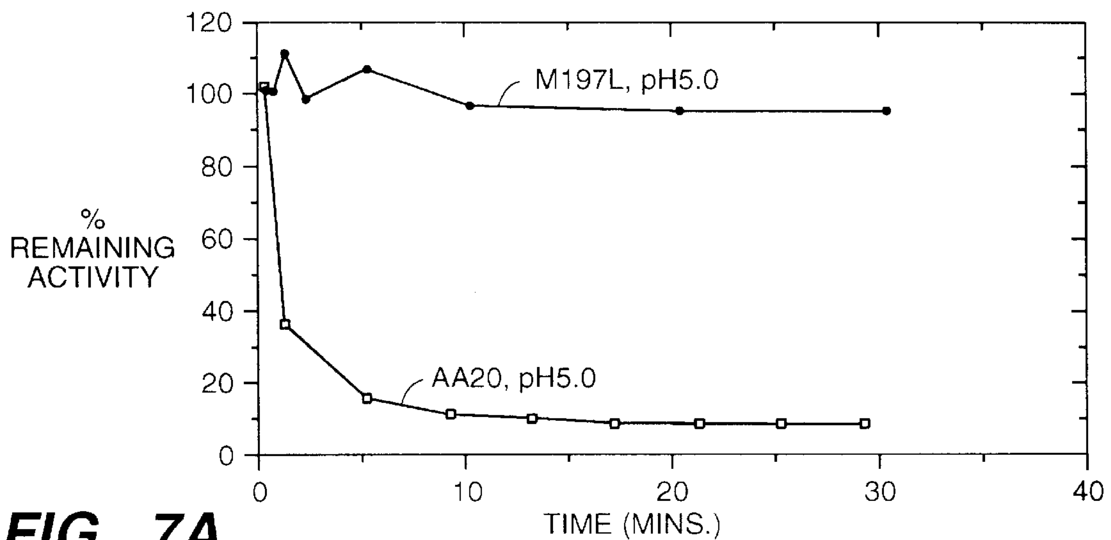
FIG._7A
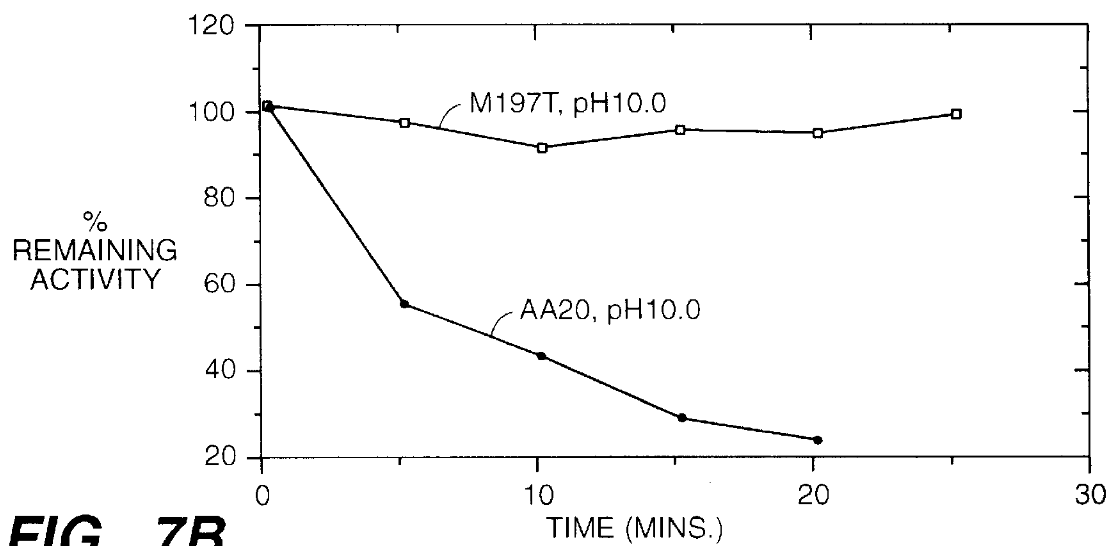
FIG._7B
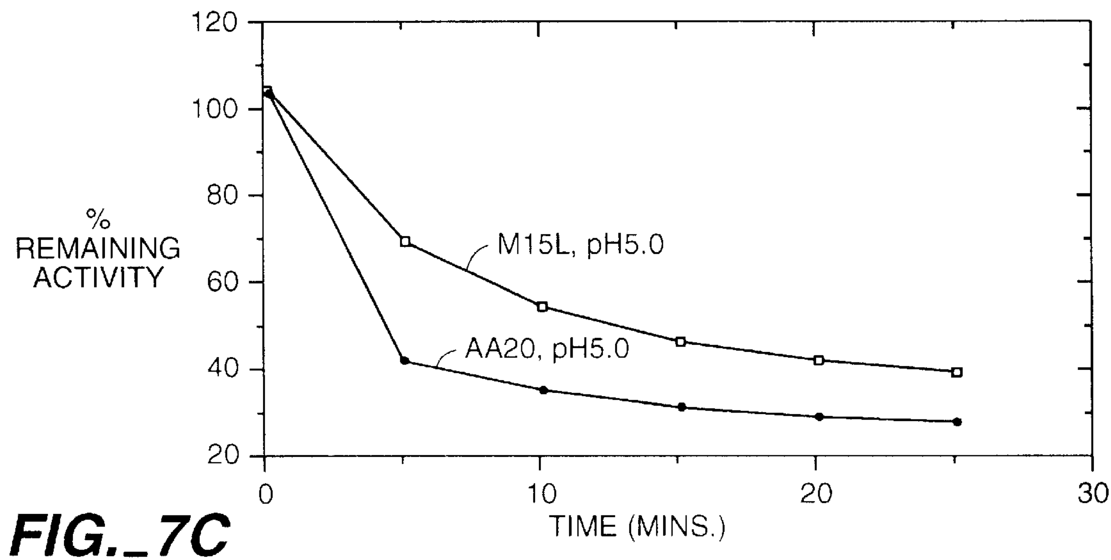
FIG._7C

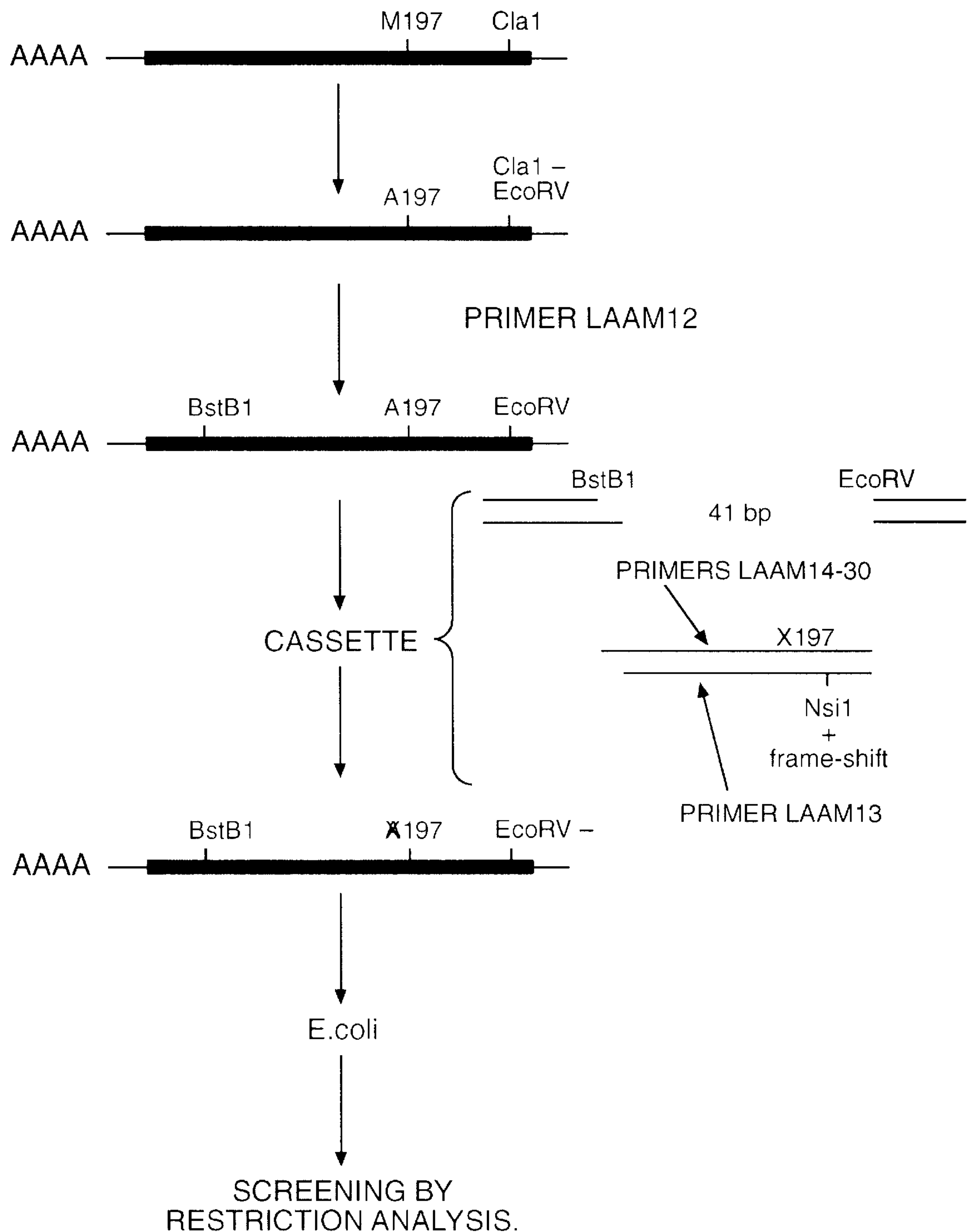
FIG._8

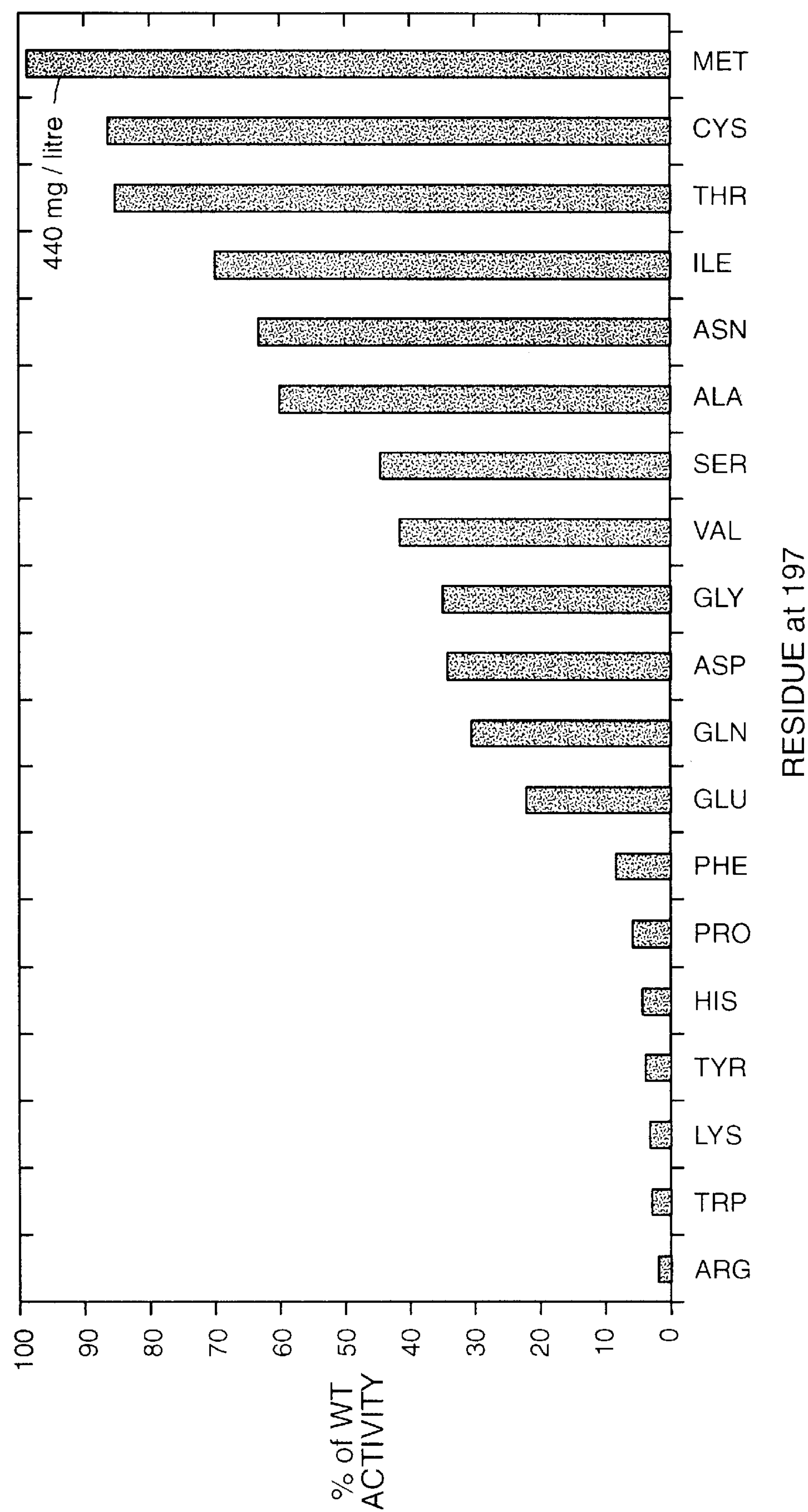
FIG._9

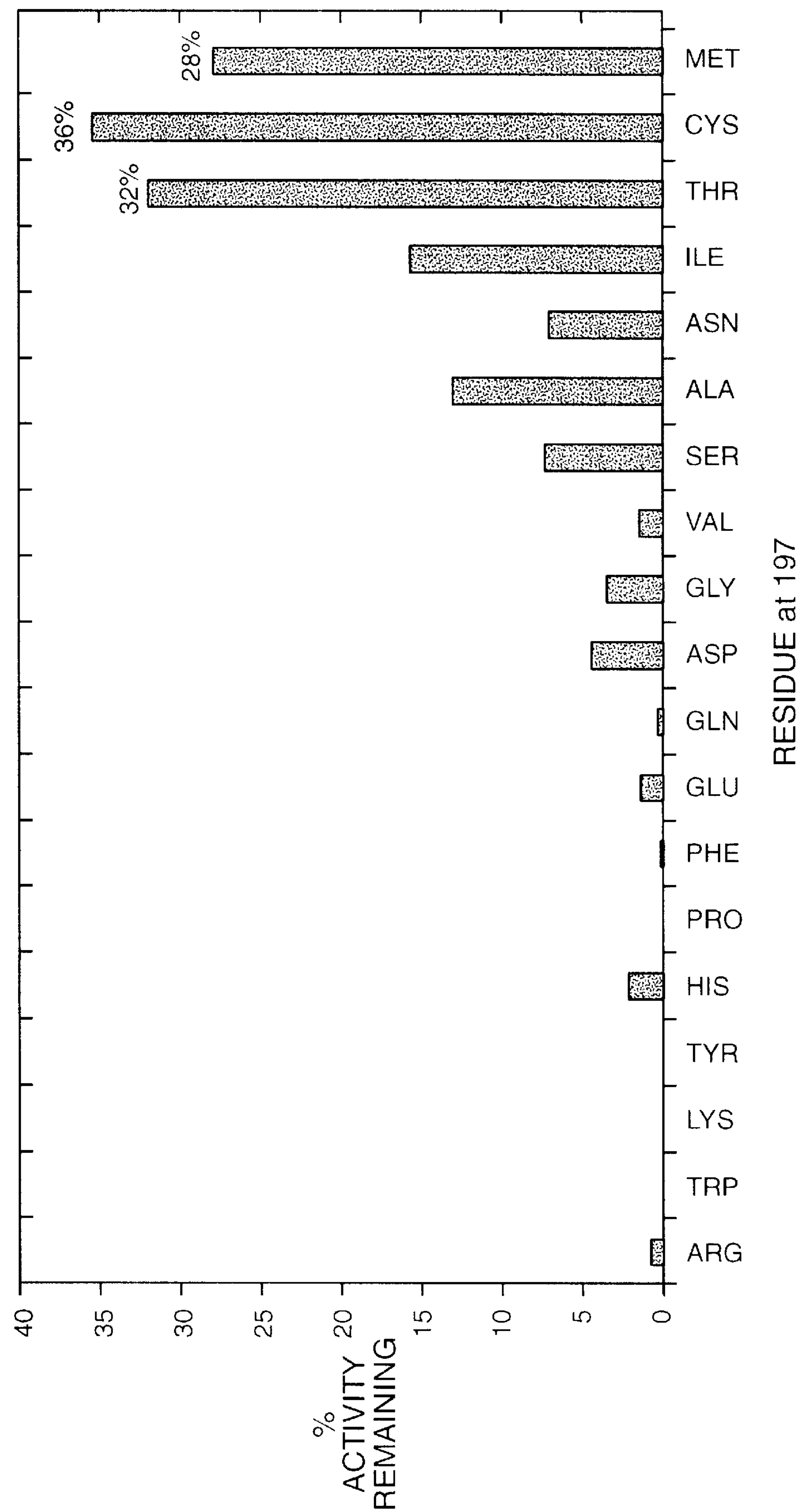
FIG._10

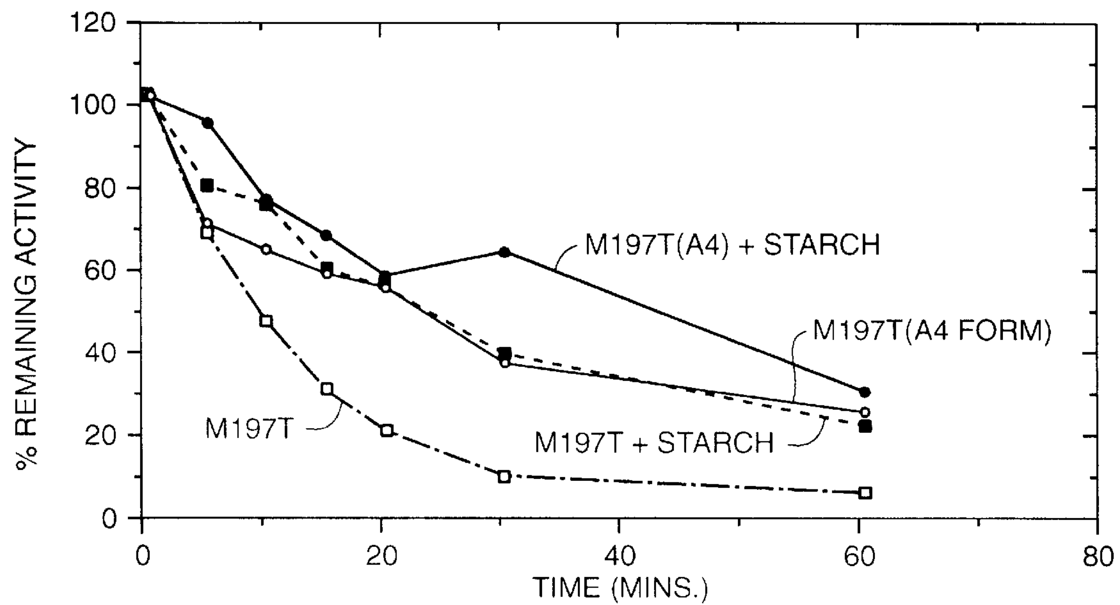
FIG._11A
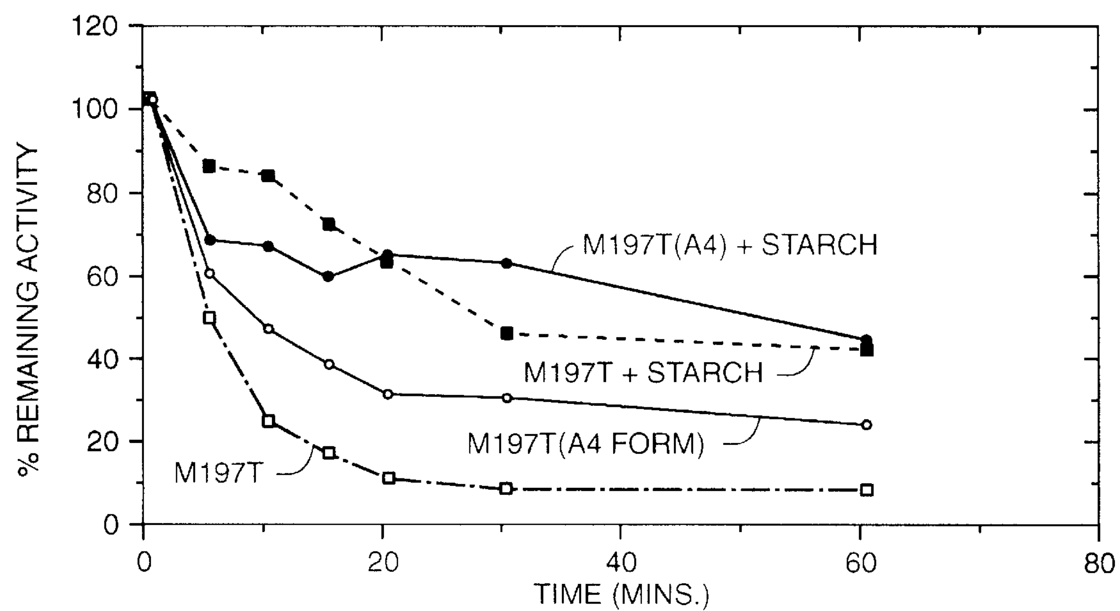
FIG._11B

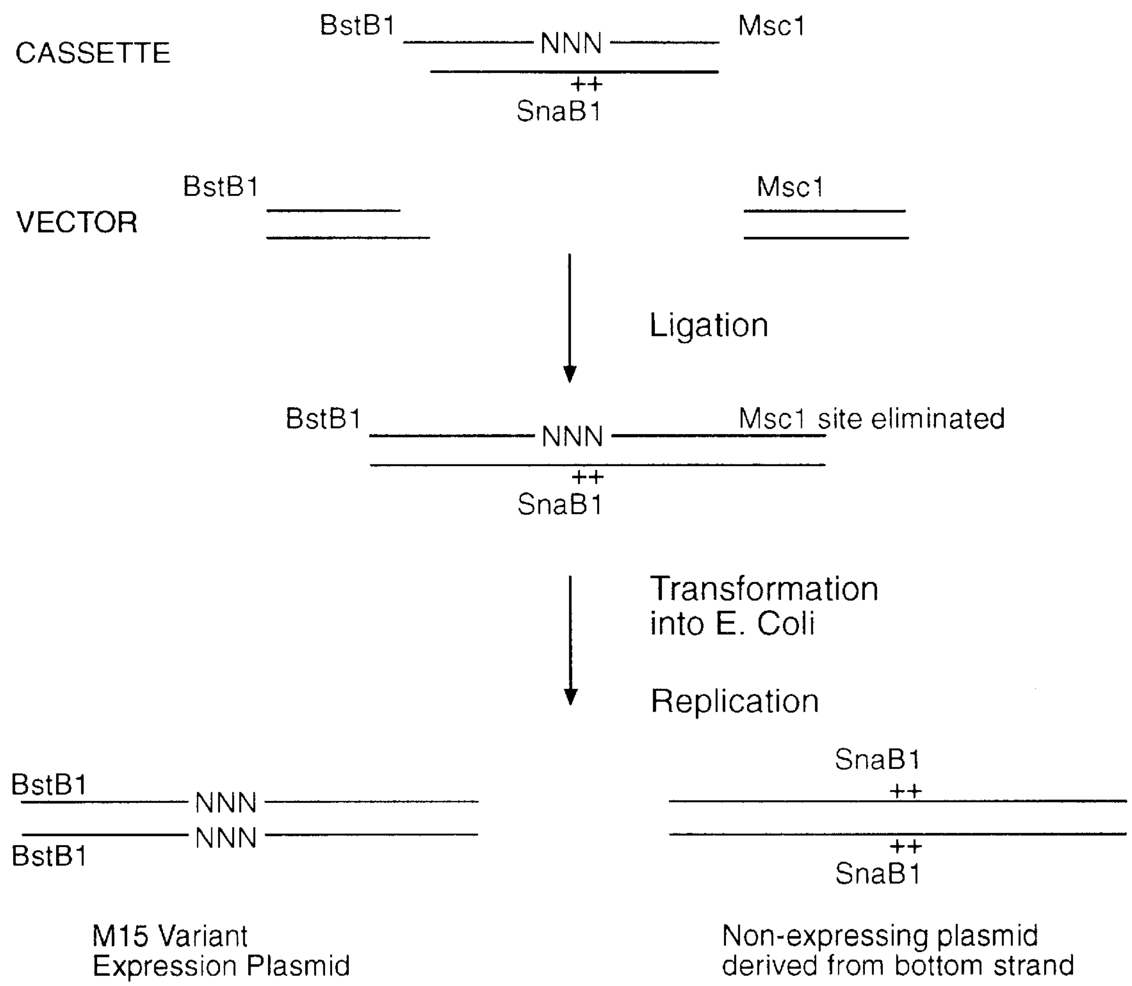
FIG._12

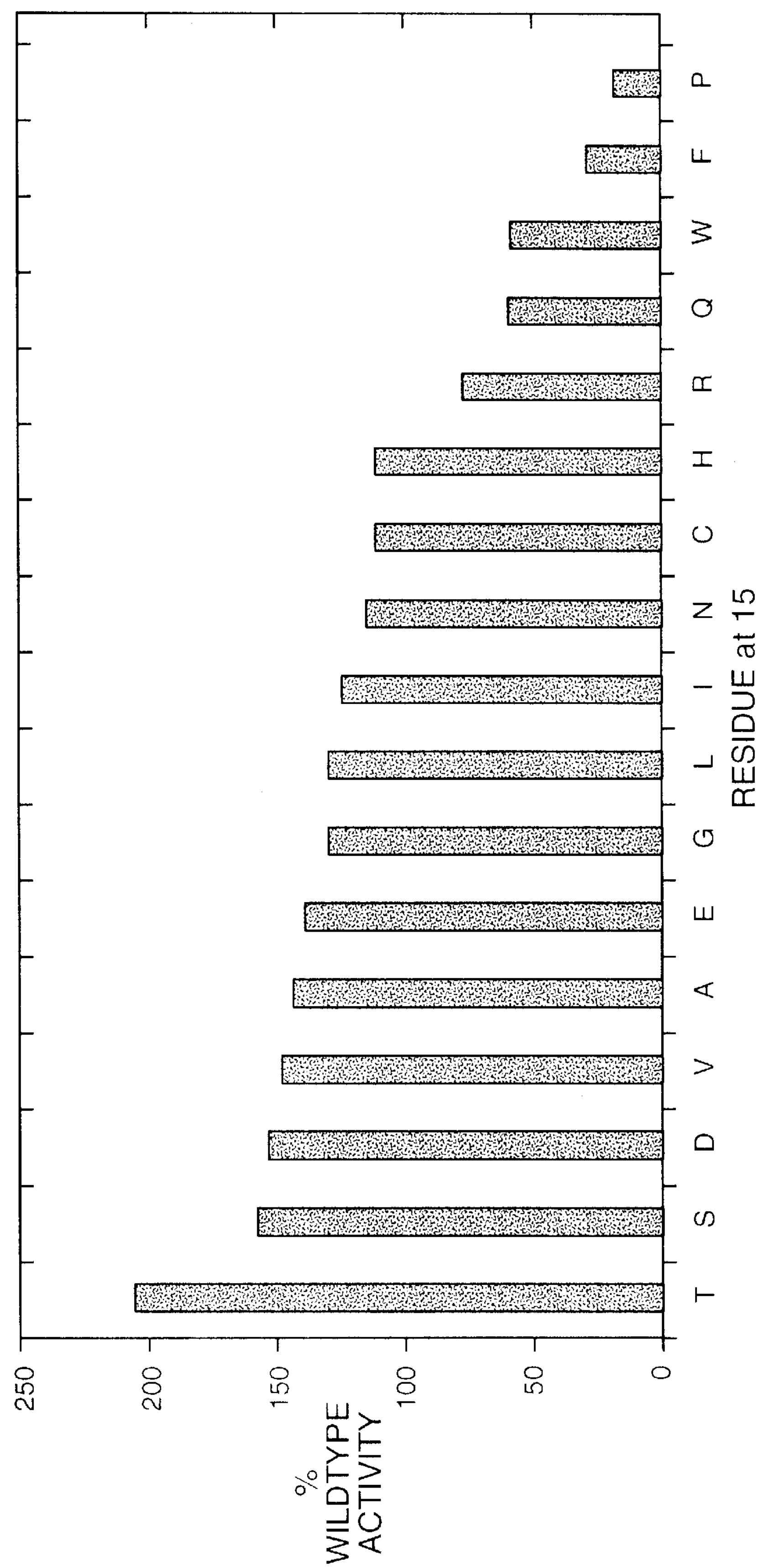
FIG._13

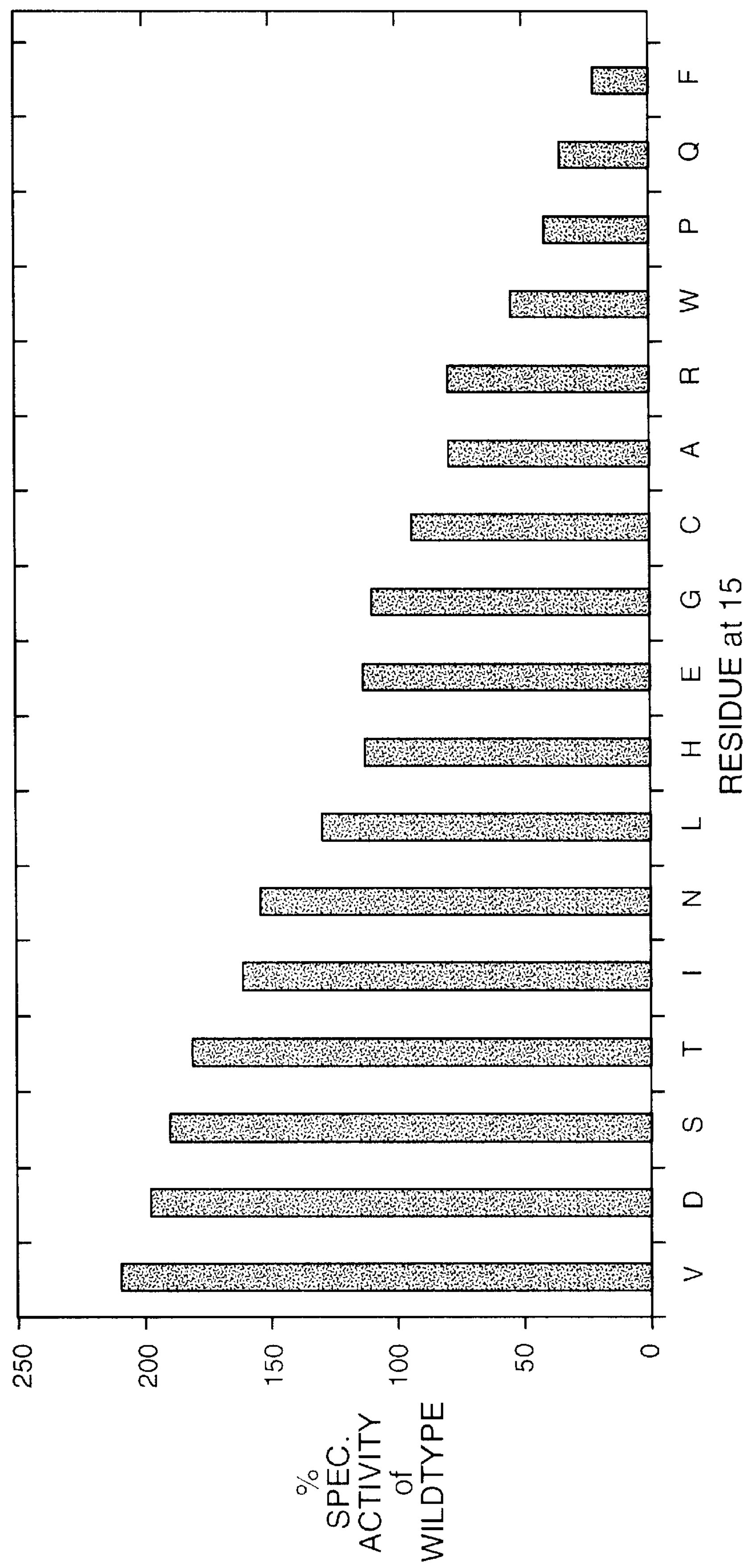
*FIG._14*

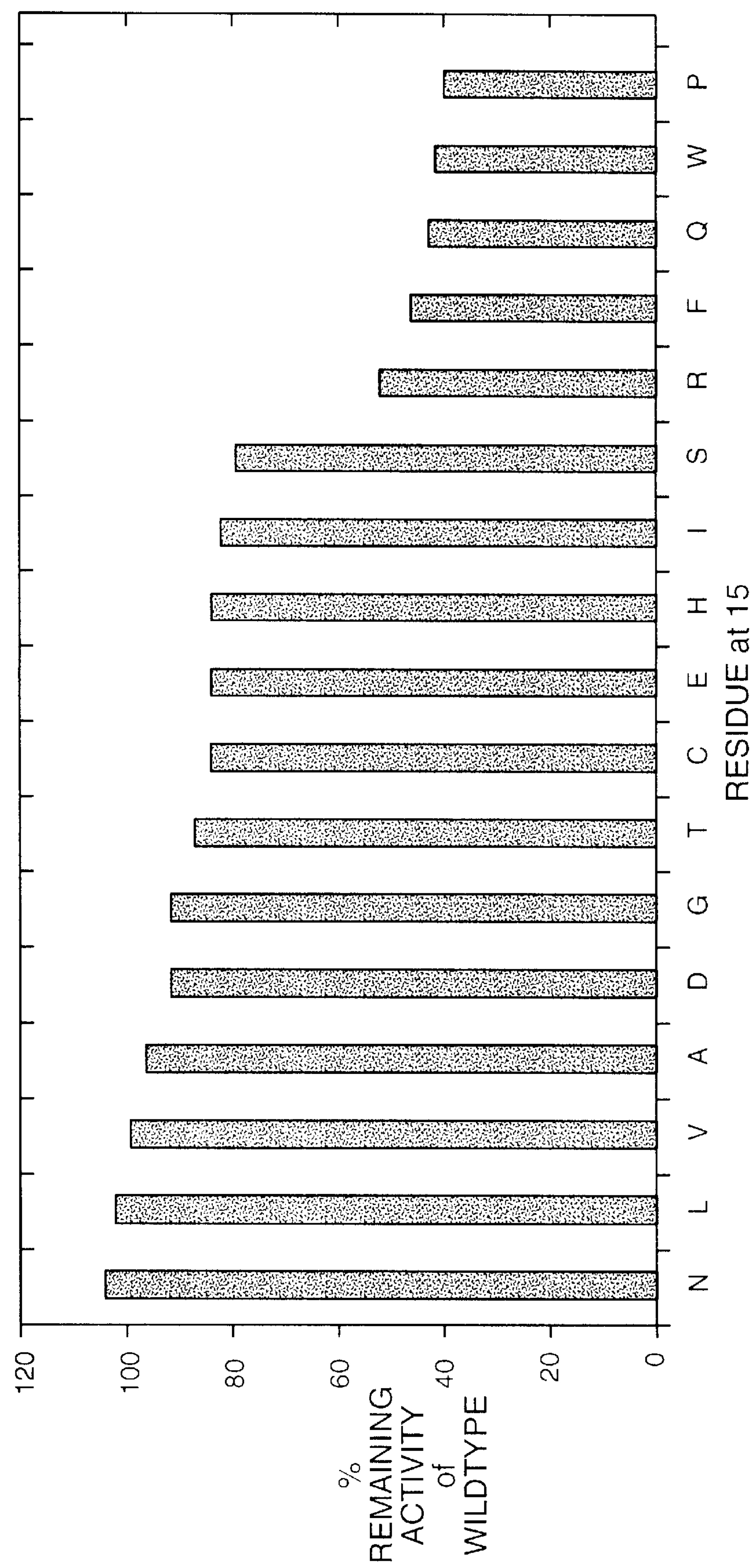
FIG._15

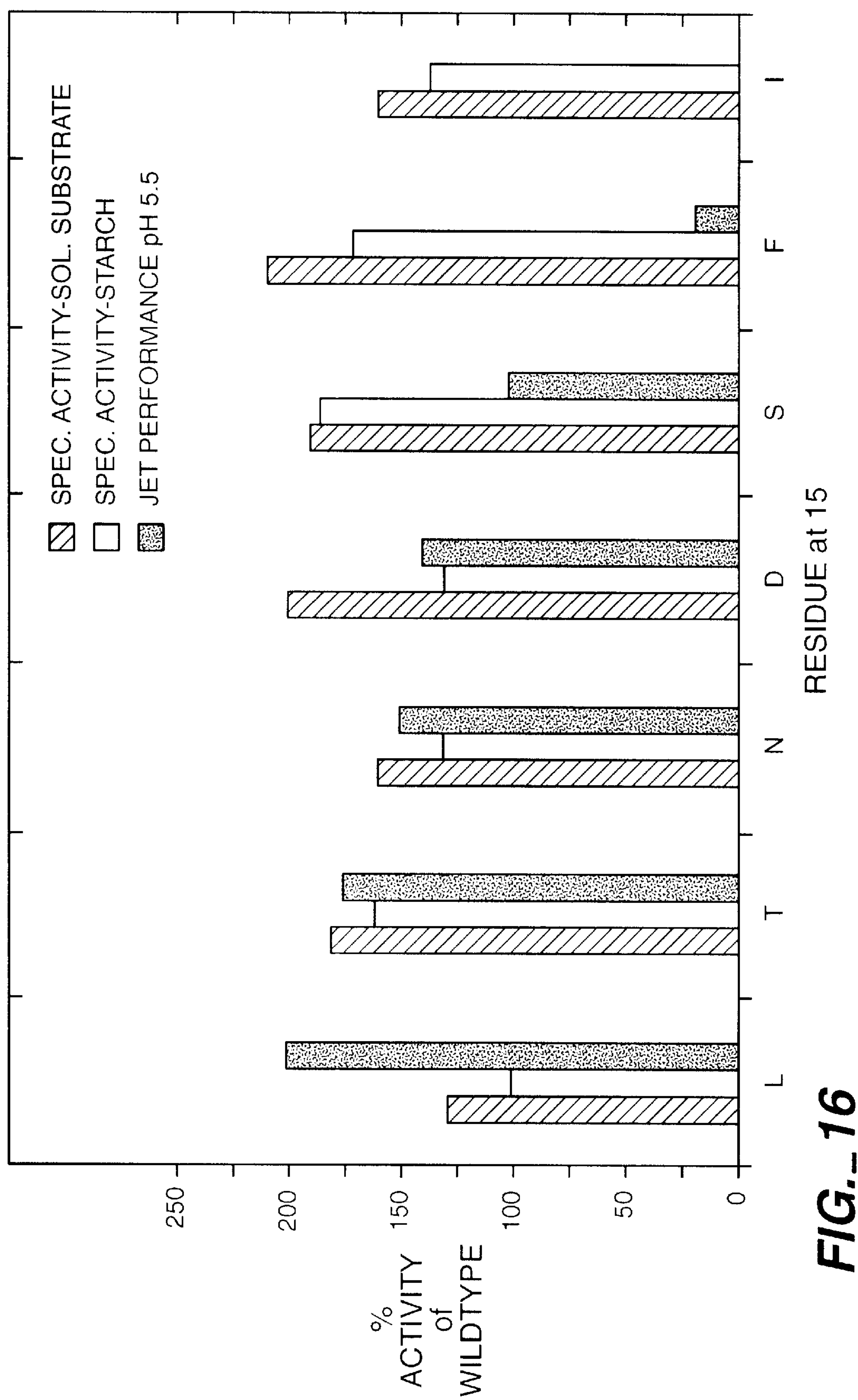
FIG._16

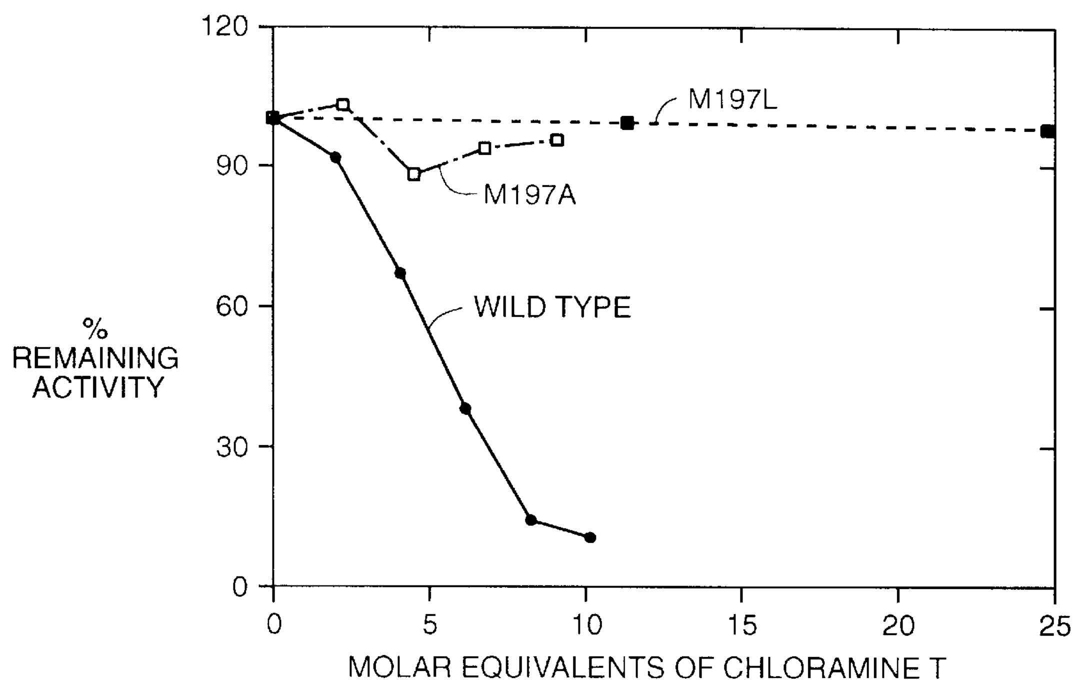
FIG._17
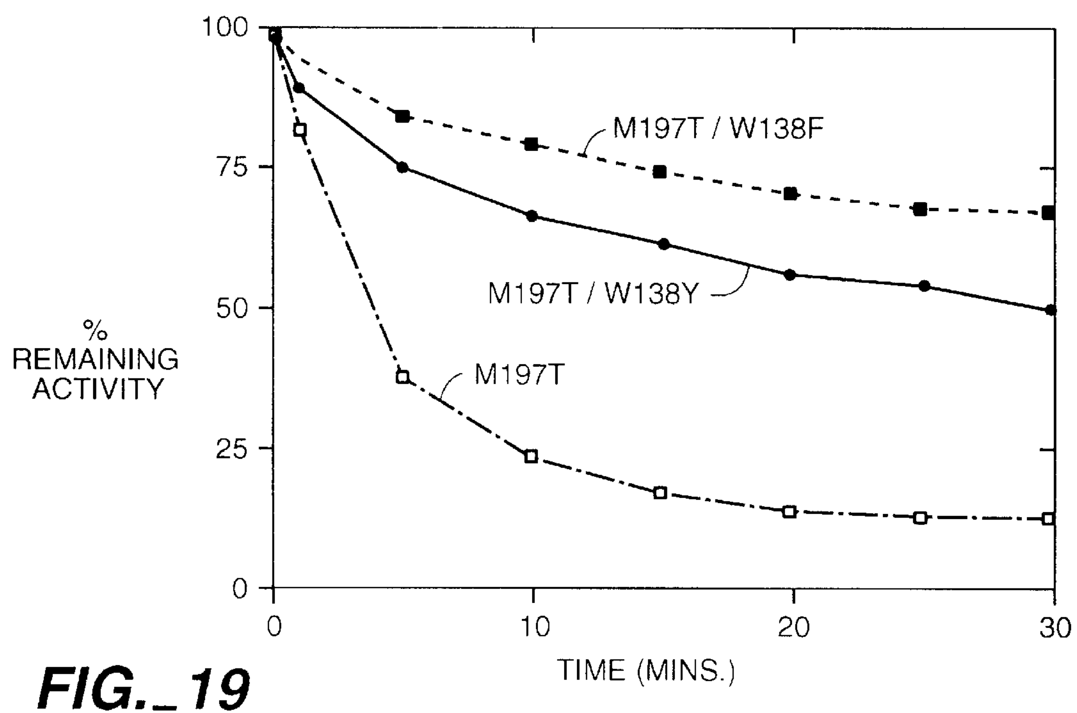
FIG._19

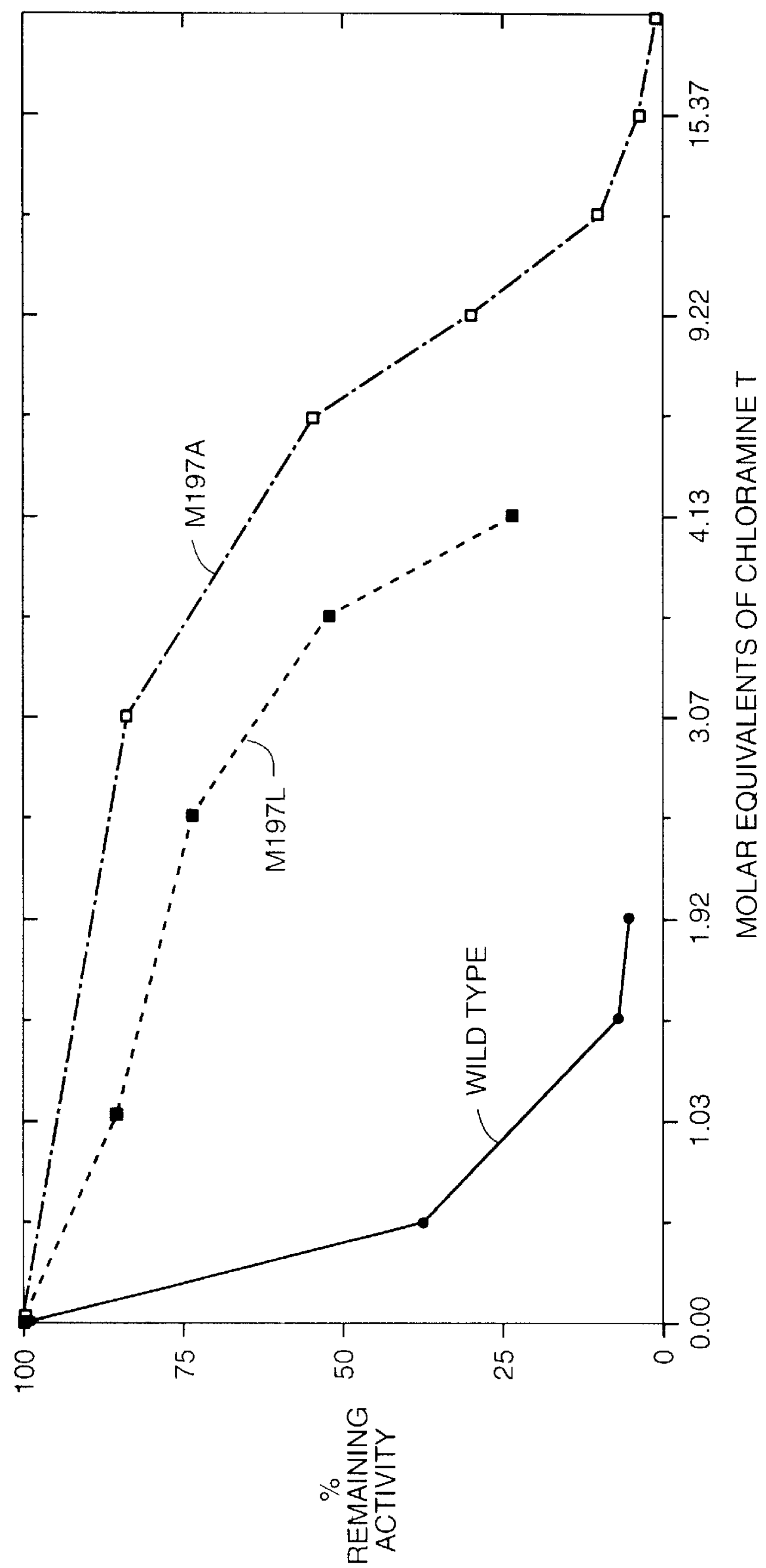
FIG._18

OXIDATIVELY STABLE ALPHA-AMYLASE

RELATED APPLICATION

This is a divisional of U.S. Ser. No. 08/194,664 filed Feb. 10, 1994, now pending, which is a continuation-in-part of U.S. Ser. No. 08/016,395 filed Feb. 11, 1993, abandoned.

FIELD OF THE INVENTION

The present invention relates to novel alpha-amylase mutants having an amino acid sequence not found in nature, such mutants having an amino acid sequence wherein one or more amino acid residue(s) of a precursor alpha-amylase, specifically any oxidizable amino acid, have been substituted with a different amino acid. The mutant enzymes of the present invention exhibit altered stability/activity profiles including but not limited to altered oxidative stability, altered pH performance profile, altered specific activity and/or altered thermostability.

BACKGROUND OF THE INVENTION

Alpha-amylases (alpha-1,4-glucan-4-glucanohydrolase, EC3.2.1.1) hydrolyze internal alpha-1,4-glucosidic linkages in starch largely at random, to produce smaller molecular weight malto-dextrins. Alpha-amylases are of considerable commercial value, being used in the initial stages (liquefaction) of starch processing; in alcohol production; as cleaning agents in detergent matrices; and in the textile industry for starch desizing. Alpha-amylases are produced by a wide variety of microorganisms including Bacillus and Aspergillus, with most commercial amylases being produced from bacterial sources such as *B. licheniformis, B. amyloliquefaciens, B. subtilis*, or *B. stearothermophilus*. In recent years the preferred enzymes in commercial use have been those from *B. licheniformis* because of their heat stability and performance, at least at neutral and mildly alkaline pH's.

Previously there have been studies using recombinant DNA techniques to explore which residues are important for the catalytic activity of amylases and/or to explore the effect of modifying certain amino acids within the active site of various amylases (Vihinen, M. et al. (1990) J. Bichem. 107:267–272; Holm, L. et al. (1990) Protein Engineering 3:181–191; Takase, K. et al. (1992) Biochemica et Biophysica Acta, 1120:281–288; Matsui, I. et al. (1992) Febs Letters Vol. 310, No. 3, pp. 216–218); which residues are important for thermal stability (Suzuki, Y. et al. (1989) J. Biol. Chem. 264:18933–18938); and one group has used such methods to introduce mutations at various histidine residues in a *B. licheniformis* amylase, the rationale for making substitutions at histidine residues was that *B. lichenffonnis* amylase (known to be thermostable) when compared to other similar Bacillus amylases, has an excess of histidines and, therefore, it was suggested that replacing a histidine could affect the thermostability of the enzyme (Declerck, N. et al. (1990) J. Biol. Chem. 265:15481–15488; FR 2 665 178-A1; Joyet, P. et al. (1992) Bio/Technology 10:1579–1583).

It has been found that alpha-amylase is inactivated by hydrogen peroxide and other oxidants at pH's between 4 and 10.5 as described in the examples herein. Commercially, alpha-amylase enzymes can be used under dramatically different conditions such as both high and low pH conditions, depending on the commercial application. For example, alpha-amylases may be used in the liquefaction of starch, a process preferably performed at a low pH (pH <5.5). On the other hand, amylases may be used in commercial dish care or laundry detergents, which often contain oxidants such as bleach or peracids, and which are used in much more alkaline conditions.

In order to alter the stability or activity profile of amylase enzymes under varying conditions, it has been found that selective replacement, substitution or deletion of oxidizable amino acids, such as a methionine, tryptophan, tyrosine, histidine or cysteine, results in an altered profile of the variant enzyme as compared to its precursor. Because currently commercially available amylases are not acceptable (stable) under various conditions, there is a need for an amylase having an altered stability andlor activity profile. This altered stability (oxidative, thermal or pH performance profile) can be achieved while maintaining adequate enzymatic activity, as compared to the wild-type or precursor enzyme. The characteristic affected by introducing such mutations may be a change in oxidative stability while maintaining thermal stability or vice versa. Additionally, the substitution of different amino acids for an oxidizable amino acids in the alpha-amylase precursor sequence or the deletion of one or more oxidizable amino acid(s) may result in altered enzymatic activity at a pH other than that which is considered optimal for the precursor alpha-amylase. In other words, the mutant enzymes of the present invention may also have altered pH performance profiles, which may be due to the enhanced oxidative stability of the enzyme.

SUMMARY OF THE INVENTION

The present invention relates to novel alpha-amylase mutants that are the expression product of a mutated DNA sequence encoding an alpha-amylase, the mutated DNA sequence being derived from a precursor alpha-amylase by the deletion or substitution (replacement) of one or more oxidizable amino acid. In one preferred embodiment of the present invention the mutant result from substituting a different amino acid for one or more methionine residue(s) in the precursor alpha-amylase. In another embodiment of the present invention the mutants comprise a substitution of one or more tryptophan residue alone or in combination with the substitution of one or more methionine residue in the precursor alpha-amylase. Such mutant alpha-amylases, in general, are obtained by in vitro modification of a precursor DNA sequence encoding a naturally occurring or recombinant alpha-amylase to encode the substitution or deletion of one or more amino acid residues in a precursor amino acid sequence.

Preferably the substitution or deletion of one or more amino acids in the amino acid sequence is due to the replacement or deletion of one or more methionine, tryptophan, cysteine, histidine or tyrosine residues in such sequence, most preferably the residue which is changed is a methionine residue. The oxidizable amino acid residues may be replaced by any of the other 20 naturally occurring amino acids. If the desired effect is to alter the oxidative stability of the precursor, the amino acid residue may be substituted with a non-oxidizable amino acid (such as alanine, arginine, asparagine, aspartic acid, glutamic acid, glutamine, glycine, isoleucine, leucine, tysine, phenylalanine, proline, serine, threonine, or valine) or another oxidizable amino acid (such as cysteine, methionine, tryptophan, tyrosine or histidine, listed in order of most easily oxidizable to less readily oxidizable). Likewise, if the desired effect is to alter thernostability, any of the other 20 naturally occurring amino acids may be substituted (i.e., cysteine may be substituted for methionine).

Preferred mutants comprise the substitution of a methionine residue equivalent to any of the methionine residues found in *B. licheniformis* alpha-amylase (+8, +15, +197, +256, +304, +366 and +438). Most preferably the methionine to be replaced is a methionine at a position equivalent to position +197 or +15 in *B. licheniforrnis* alpha-amylase. Preferred substitute amino acids to replace the methionine at position +197 are alanine (A), isoleucine (I), threonine (T) or cysteine (C). The preferred substitute amino acids at position +15 are leucine (L), threonine (T), asparagine (N), aspartate (D), serine (S), valine (V) and isoleucine (I), although other substitute amino acids not specified above may be useful. Two specifically preferred mutants of the present invention are M197T and M15L.

Another embodiment of this invention relates to mutants comprising the substitution of a tryptophan residue equivalent to any of the tryptophan residues found in *B. licheniforrnis* alpha-amylase (see FIG. 2). Preferably the tryptophan to be replaced is at a position equivalent to +138 in *B. licheniformis* alpha-amylase. A mutation (substitution) at a tryptophan residue may be made alone or in combination with mutations at other oxidizable amino acid residues. Specifically, it may be advantageous to modify by substitution at least one tryptophan in combination with at least one methionine (for example, the double mutant +138/+197).

The alpha-amylase mutants of the present invention, in general, exhibit altered oxidative stability in the presence of hydrogen peroxide and other oxidants such as bleach or peracids, or, more specific, milder oxidants such as chloramine-T. Mutant enzymes having enhanced oxidative stability will be useful in extending the shelf life and bleach, perborate, percarbonate or peracid compatibility of amylases used in cleaning products. Similarly, reduced oxidative stability may be useful in industrial processes that require the rapid and efficient quenching of enzymatic activity. The mutant enzymes of the present invention may also demonstrate a broadened pH performance profile whereby mutants such as M15L show stability for low pH starch liquefaction and mutants such as M197T show stability at high pH cleaning product conditions. The mutants of the present invention may also have altered thermal stability whereby the mutant may have enhanced stability at either high or low temperatures. It is understood that any change (increase or decrease) in the mutant's enzymatic characteristic(s), as compared to its precursor, may be beneficial depending on the desired end use of the mutant alpha-amylase.

In addition to starch processing and cleaning applications, variant amylases of the present invention may be used in any application in which known amylases are used, for example, variant amylases can be used in textile processing, food processing, etc. Specifically, it is contemplated that a variant enzyme such as M197C, which is easily inactivated by oxidation, would be useful in a process where it is desirable to completely remove amylase activity at the end oftoe process, for example, in frozen food processing applications.

The preferred alpha-amylase mutants of the present invention are derived from a Bacillus strain such as *B. licheniformis*, *B. amyloliquefaciens*, and *B. stearothermophilus*, and most preferably from *Bacillus licheniformis*.

In another aspect of the present invention there is provided a novel form of the alpha-amylase normally produced by *B. licheniformis*. This novel form, designated as the A4 form, has an additional four alanine residues at the N-terminus of the secreted amylase. (FIG. 4*b*.) Derivatives or mutants of the A4 form of alpha-amylase are encompassed within the present invention. By derivatives or mutants of the A4 form, it is meant that the present invention comprises the A4 form alpha-amylase containing one or more additional mutations such as, for example, mutation (substitution, replacement or deletion) of one or more oxidizable amino acid(s).

In a composition embodiment of the present invention there are provided detergent compositions, liquid, gel or granular, comprising the alpha-amylase mutants described herein. Particularly preferred are detergent compositions comprising a +197 position mutant either alone or in combination with other enzymes such as endoglycosidases, cellulases, proteases, lipases or other amylase enzymes. Additionally, it is contemplated that the compositions of the present invention may include an alpha-amylase mutant having more than one site-specific mutation.

In yet another composition embodiment of the present invention there are provided compositions useful in starch processing and particularly starch liquefaction. The starch liquefaction composition of the present invention preferably comprise an alpha-amylase mutant having a substitution or deletion at position M15. Additionally, it is contemplated that such compositions may comprise additional components as known to those skilled in the art, including, for example, antioxidants, calcium, ions, etc.

In a process aspect of the present invention there are provided methods for liquefying starch, and particularly granular starch slurries, from either a wet or dry milled process. Generally, in the first step of the starch degradation process, the starch slurry is gelatinized by heating at a relatively high temperature (up to about 110° C.). After the starch slurry is gelatinized it is liquefied and dextrinized using an alpha-amylase. The conditions for such liquefaction are described in commonly assigned U.S. patent application Ser. Nos. 07/785,624 and 07/785,623 and U.S. Pat. No. 5,180,669, the disclosure of which are incorporated herein by reference. The present method for liquefying starch comprises adding to a starch slurry an effective amount of an alpha-amylase of the present invention, alone or in combination with additional excipients such as an antioxidant, and reacting the slurry for an appropriate time and temperature to liquefy the starch.

A further aspect of the present invention comprises the DNA encoding the mutant alpha-amylases of the present invention (including A4 form and mutants thereof) and expression vectors encoding the DNA as well as host cells transformed with such expression vectors.

BRIEF DESCRIPTION OF THE DRAWINGS

FIG. 1 shows the DNA sequence of the gene for alpha-amylase from *B. licheniformis* (NCIB8061), Seq ID No 31, and deduced translation product as described in Gray, G. et al. (1986) J. Bacter. 166:635–643.

FIG. 2 shows the amino acid sequence of the mature alpha-amylase enzyme from *B. licheniformis* (NCIB8061), Seq ID No 32.

FIG. 3 shows an alignment of primary structures of Bacillus alpha-amylases. The *B. licheniformis* amylase (Am-Lich), Seq ID No 33, is described by Gray, G. et al. (1986) J. Bact. 166:635–643; the *B. amyloliquefaciens* amylase (Am-Amylo), Seq ID No 34, is described by Takkinen, K. et al. (1983) J. Biol. Chem. 258:1007–1013; and the *B. stearothermophilus* (Am-Stearo), Seq ID No 35, is described by Ihara, H. et al. (1985) J. Biochem. 98:95–103.

FIG. 4*a* shows the amino acid sequence of the mature alpha-amylase variant M197T, Seq ID No 36.

FIG. 4*b* shows the amino acid sequence of the A4 form of alpha-amylase from *B. licheniformis* NCIB8061, Seq ID No 37. Numbering is from the N-terminus, starting with the four additional alanines.

FIG. 5 shows plasmid pA4BL wherein BLAA refers to *B. licheniformis* alpha-amylase gene, PstI to SstI; $Amp^R$ refers to the ampicillin-resistant gene from pBR322; and CAT refers to the Chloramphenicol-resistant gene from pC194.

FIG. 6 shows the signal sequence-mature protein junctions for *B. licheniformis* (Seq ID No 38), *B. subtilis* (Seq ID No 39), *B. licheniformis* in pA4BL (Seq ID No 40) and *B. licheniformis* in pBLapr (Seq ID No 41).

FIG. 7*a* shows inactivation of certain alpha-amylases (Spezyme® AA20 and M197L (A4 form) with 0.88M $H_2O_2$ at pH 5.0, 25° C.

FIG. 7*b* shows inactivation of certain alpha-amylases (Spezyme® AA20, M197T) with 0.88M $H_2O_2$ at pH 10.0, 25° C.

FIG. 7*c* shows inactivation of certain alpha-amylases (Spezyme® A20, M15L) with 0.88M $H_2O_2$ at pH 5.0, 25° C.

FIG. 8 shows a schematic for the production of M197X cassette mutants.

FIG. 9 shows expression of M197X variants.

FIG. 10 shows thermal stability of M197X variants at pH 5.0, 5 mM $CaCl_2$ at 95° C. for 5 mins.

FIGS. 11*a* and 11*b* show inactivation of certain amylases in automatic dish care detergents.

FIG. 11*a* shows the stability of certain amylases in Cascade™ (a commercially available dish care product) at 65° C. in the presence or absence of starch. FIG. 11*b* shows the stability of Certain amylases in Sunlight™ (a commercially available dish care product) at 65° C. in the presence or absence of starch.

FIG. 12 shows a schematic for the production of M15X cassette mutants.

FIG. 13 shows expression of M15X variants.

FIG. 14 shows specific activity of M15X variants on soluble stach.

FIG. 15 shows heat stability of M15X variants at 90° C., pH 5.0, 5 mM $CaCl_2$, 5 mins.

FIG. 16 shows specific activity on starch and soluble substrate, and performance in jet liquefaction at pH 5.5, of M15 variants as a function of percent activity of *B. licheniformis* wild-type.

FIG. 17 shows the inactivation of *B. licheniformis* alpha-amylase (AA20 at 0.65 mg/ml) with chloraminon-T at pH 8.0 as compared to variants M197A (1.7 mg/ml) and M197L (1.7 mg/ml).

FIG. 18 shows the inactivation of *B. licheniformis* alpha-amylase (AA20 at 0.22 mg/ml) with chloramine-T at pH 4.0 as compared to variants M197A (4.3 mg/ml) and M197L (0.53 mg/ml).

FIG. 19 shows the reaction of *B. licheniformis* alpha-amylase (AA20 at 0.75 mg/ml) with chloramine-T at pH 5.0 as compared to double variants M197T/W138F (0.64 mg/ml) and M197T/W138Y (0.60 mg/ml).

DETAILED DESCRIPTION OF THE INVENTION

It is believed that amylases used in starch liquefaction may be subject to some form of inactivation due to some activity present in the starch slurry (see commonly owned U.S. application Ser. Nos. 07/785,624 and 071785,623 and U.S. Pat. No. 5,180,669, issued Jan. 19, 1993, incorporated herein by reference). Furthermore, use of an amylase in the presence of oxidants, such as in bleach or peracid containing detergents, may result in partial or complete inactivation of the amylase. Therefore, the present invention focuses on altering the oxidative sensitivity of amylases. The mutant enzymes of the present invention may also have an altered pH profile and/or altered thermal stability which may be due to the enhanced oxidative stability of the enzyme at low or high pH's.

Alpha-amylase as used herein includes naturally occurring amylases as well as recombinant amylases. Preferred amylases in the present invention are alpha-amylases derived from *B. licheniformis* or *B. stearothermophilus*, including the A4 form of alpha-amylase derived from *B. licheniformis* as described herein, as well as fungal alpha-amylases such as those derived from Aspergillus (i.e., *A. oryzae* and *A. niger*).

Recombinant alpha-amylases refers to an alpha-amylase in which the DNA sequence encoding the naturally occurring alpha-amylase is modified to produce a mutant DNA sequence which encodes the substitution, insertion or deletion of one or more amino acids in the alpha-amylase sequence. Suitable modification methods are disclosed herein, and also in commonly owned U.S. Pat. Nos. 4,760,025 and 5,185,258, the disclosure of which are incorporated herein by reference.

Homologies have been found between almost all endoamylases sequenced to date, ranging from plants, mammals, and bacteria (Nakajima, R. T. et al. (1986) Appl. Microbiol. Biotechnol. 23:355–360; Rogers, J. C. (1985) Biochem. Biophys. Res. Commun. 128:470–476). There are four areas of particularly high homology in certain Bacillus amylases, as shown in FIG. 3, wherein the underlined sections designate the areas of high homology. Further, sequence alignments have been used to map the relationship between Bacilus endo-amylases (Feng, D. F. and Doolittle, R. F. (1987) J. Molec. Evol. 35:351–360). The relative sequence homology between *B. stearothermophilus* and *B. licheniformis* amylase is about 66%, as determined by Holm, L. et al. (1990). Protein Engineering 3 (3) pp. 181–191. The sequence homology between *B. licheniformis* and *B. amyloliquefaciens* amylases is about 81%, as per Holm, L. et al., supra. While sequence homology is important, it is generally recognized that structural homology is also important in comparing amylases or other enzymes. For example, structural homology between fungal amylases and bacterial (Bacillus) amylase have been suggested and, therefore, fungal amylases are encompassed within the present invention.

An alpha-amylase mutant has an amino acid sequence which is derived from the amino acid sequence of a precursor alpha-amylase. The precursor alpha-amylases include naturally occurring alpha-amylases and recombinant alpha-amylases (as defined). The amino acid sequence of the alpha-amylase mutant is derived from the precursor alpha-amylase amino acid sequence by the substitution, deletion or insertion of one or more amino acids of the precursor amino acid sequence. Such modification is of the precursor DNA sequence which encodes the amino acid sequence of the precursor alpha-amylase rather than manipulation of the precursor alpha-amylase enzyme per se. Suitable methods for such manipulation of the precursor DNA sequence include methods disclosed herein and in commonly owned U.S. Pat. Nos. 4,760,025 and 5,185,258.

Specific residues corresponding to positions M197, M15 and W138 of *Bacillus licheniformis* alpha-amylase are identified herein for substitution or deletion, as are all methionine, histidine, tryptophan, cysteine and tymsine positions. The amino acid position number (i.e., +197) refers to the number assigned to the mature *Bacillus licheniformis* alpha-amylase sequence presented in FIG. 2. The invention, however, is not limited to the mutation of this particular mature alpha-amylase (*B. licheniformis*) but extends to precursor alpha-amylases containing amino acid residues at positions which are equivalent to the particular identified residue in *B. licheniformis* alpha-amylase residue (amino acid) of a precursor alpha-amylase is equivalent to a residue of *B. licheniformis* alpha-amylase if it is either homologous (i.e., corresponding in position in either primary or tertiary structure) or analogous to a specific residue or portion of that residue in *B. licheniformis* alpha-amylase (i.e., having the same or similar functional capacity to combine, react, or interact chemically or structurally).

In order to establish homology to primary structure, the amino acid sequence of a precursor alpha-amylase is directly compared to the *B. licheniformis* alpha-amylase primary sequence and particularly to a set of residues known to be invariant to all alpha-amylases for which sequence is known, as seen in FIG. 3. It is possible also to determine equivalent residues by tertiary structure: crystal structures have been reported for porcine pancreatic alpha-amylase (Buisson, G. et al. (1987) EMBO J.6:3909–3916); Taka-amylase A from *Aspergillus oryzae* (Matsuura, Y. et al. (1984) J. Biochem. (Tokyo) 95:697–702); and an acid alpha-amylase from *A. niger* (Boel, E. et al. (1990) Biochemistry 29:6244–6249), with the former two structures being similar. There are no published structures for Bacillus alpha-amylases, although there are predicted to be common super-secondary structures between glucanases (MacGregor, E. A. & Svensson, B. (1989) Biochem. J. 259:145–152) and a structure for the *B. stearothermophilus* enzyme has been modeled on that of Taka-amylase A (Holm, L. et al. (1990) Protein Engineering 3:181–191). The four highly conserved regions shown in FIG. 3 contain many residues thought to be part of the active-site (Matsuura, Y. et al. (1984) J. Biochem. (Tokyo) 95:697–702; Buisson, G. et al. (1987) EMBO J. 6:3909–3916; Vihinen, M. et al. (1990) J. Biochem. 107:267–272) including, in the licheniformis numbering, His105; Arg229; Asp231; His235; Glu261 and Asp328.

Expression vector as used herein refers to a DNA construct containing a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *B. subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

Host strains (or cells) useful in the present invention generally are procaryotic or eucaryotic hosts and include any transformable microorganism in which the expression of alpha-amylase can be achieved. Specifically, host strains of the same species or genus from which the alpha-amylase is derived are suitable, such as a Bacillus strain. Preferably an alpha-amylase negative Bacillus strain (genes deleted) and/or an alpha-amylase and protease deleted Bacillus strain such as *Bacillus subtilis* strain BG2473 (ΔamyE,Δapr,Δnpr) is used. Host cells are transformed or transfected with vectors constructed using recombinant DNA techniques. Such transformed host cells are capable of either replicating vectors encoding the alpha-amylase and its variants (mutants) or expressing the desired alpha-amylase.

Preferably the mutants of the present invention are secreted into the culture medium during fermentation. Any suitable signal sequence, such as the aprE signal peptide, can be used to achieve secretion.

Many of the alpha-amylase mutants of the present invention are useful in formulating various detergent compositions, particularly certain dish care cleaning compositions, especially those cleaning compositions containing known oxidants. Alpha-amylase mutants of the invention can be formulated into known powdered, liquid or gel detergents having pH between 6.5 to 12.0. Suitable granular composition may be made as described in commonly owned U.S. patent application Ser. Nos. 07/429,881, 07/533,721 and 07/957,973, all of which are incorporated herein by reference. These detergent cleaning compositions can also contain other enzymes, such as known proteases, lipases, cellulases, endoglycosidases or other amylases, as well as builders, stabilizers or other excipients known to those skilled in the art. These enzymes can be present as co-granules or as blended mixes or in any other manner known to those skilled in the art. Furthermore, it is contemplated by the present invention that multiple mutants may be useful in cleaning or other applications. For example, a mutant enzyme having changes at both +15 and +197 may exhibit enhanced performance useful in a cleaning product or a multiple mutant comprising changes at +197 and +138 may have improved performance.

As described previously, alpha-amylase mutants of the present invention may also be useful in the liquefaction of starch. Starch liquefaction, particularly granular starch slurry liquefaction, is typically carried out at near neutral pH's and high temperatures. As described in commonly owned U.S. application Ser. Nos. 07/788,624 and 07/785,623 and U.S. Pat. No. 5,180,669, it appears that an oxidizing agent or inactivating agent of some sort is also present in typical liquefaction processes, which may affect the enzyme activity; thus, in these related patent applications an antioxidant is added to the process to protect the enzyme.

Based on the conditions of a preferred liquefaction process, as described in commonly owned U.S. application Ser. Nos. 071788,624 and 071785,623 and U.S. Pat. No. 5,180,669, namely low pH, high temperature and potential oxidation conditions, preferred mutants of the present invention for use in liquefaction processes comprise mutants exhibiting altered pH performance profiles (i.e., low pH profile, pH <6 and preferably pH <5.5), and/or altered thermal stability (i.e., high temperature, about 90°–110° C.), and/or altered oxidative stability (i.e., enhanced oxidative stability).

Thus, an improved method for liquefying starch is taught by the present invention, the method comprising liquefying a granular starch slurry from either a wet or dry milling process at a pH from about 4 to 6 by adding an effective amount of an alpha-amylase mutant of the present invention to the starch slurry; optionally adding an effective amount of an antioxidant or other excipient to the slurry; and reacting the slurry for an appropriate time and temperature to liquefy the starch.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

EXPERIMENTAL

Example 1

Substitutions for the Methionine Residues in *B. licheniformis* Alpha-Amylase

The alpha-amylase gene (FIG. 1) was cloned from *B. licheniformis* NCIBBD8061 obtained from the National Collection of Industrial Bacteria, Aberdeen, Scotland (Gray, G. et al. (1986) J. Bacteriology 166:635–643). The 1.72 kb PstI-SstI fragment, encoding the last three residues of the signal sequence; the entire mature protein and the terminator region was subcloned into M13MP18. A synthetic terminator was added between the BlI and SstI sites using a synthetic oligonucleotide cassette of the form:

```
BCLI                                                                   SstI
5'  GATCAAAACATAAAAAACCGGCCTTGGCCCCGCCGGTTTTTTATTATTTTTGAGCT  3'
3'      TTTTGTATTTTTTGGCCGGAACCGGGGCGGCCAAAAAATAATAAAAAC      5'
                                                           Seq ID No 1
```

designed to contain the *B. amyloliquefaciens* subtilisin transcriptional terminator (Wells et al. (1983) Nucleic Acid Research 11:7911–7925).

Site-directed mutagenesis by oligonucleotides used essentially the protocol of Zoller, M. et al. (1983) Meth. Enzymol. 100:468–500: briefly, 5'-phosphorylated oligonucleotide primers were used to introduce the desired mutations on the M13 single-stranded DNA template using the oligonucleotides listed in Table I to substitute for each of the seven methionines found in *B. licheniformis* alpha-amylase. Each mutagenic oligonucleotide also introduced a restriction endonuclease site to use as a screen for the linked mutation.

TABLE I

Mutagenic Oligonucleotides for the Substitution of the Methionine Residues in *B. licheniformis* Alpha-Amylase

| Mutation | Oligonucleotide | Site | Seq ID |
|---|---|---|---|
| M8A | 5'-T GGG ACG CTG **GC**G CAG TAC TTT GAA TGG T-3' | ScaI+ | Seq ID No 2 |
| M15L | 5'-TG ATG CAG T**AC** TTT GAA TGG TAC **C**TG CCC AAT GA-3' | ScaI+; KpnI+ | Seq ID No 3 |
| M197L | 5'-GAT TAT TTG **T**TG TAT GCC GA**T** ATC GAC TAT GAC CAT-3' | EcoRV+ | Seq ID No 4 |
| M256A | 5'-CG GGG AAG G**AG** **GCC** TTT ACG GTA GCT-3' | StuI+ | Seq ID No 5 |
| M304L | 5'-GC G GC TAT GA**C** **TTA** AGG AAA TTG C-3' | AflII+ | Seq ID No 6 |
| M366A | 5'-C TAC GGG GAT **GCA** TAC GGG ACG A-3' | NsiI+ | Seq ID No 7 |
| M366Y | 5'-C TAC GGG GAT **TAC** TAC GGG A**C**C **AAG** GGA GAC TCC C-3' | StyI+ | Seq ID No 8 |
| M438A | 5'-CC GGT GGG GC**C** AAG CG**G** **GCC** TAT GT**T** GGC CGG CAA A-3' | SfiI+ | Seq ID No 9 |

Bold letter indicate base changes introduced by oligonucleotide.
Codon changes indicated in the form M8A, where methionine (M) at position +8 has been changed to alanine (A).
Underlining indicates restriction endonuclease site introduced by oligonucleotide.

The heteroduplex was used to transfect *E. coli* mutL cells (Kramer et al. (1984) Cell 38:879) and, after plaque-purification, clones were analyzed by restriction analysis of the RF1's. Positives were confirmed by dideoxy sequencing (Sanger et al. (1977) Proc. Natl. Acad. Sci. U.S.A. 7:5463–5467) and the PstI-SstI fragments for each subcloned into an *E. coil* vector, plasmid pA4BL.

Plasmid pA4BL

Following the methods described in U.S. application Ser. No. 860,468 (Power et al.), which is incorporated herein by reference, a silent Pstl site was introduced at codon +1 (the first amino-acid following the signal cleavage site) of the aprE gene from pS168-1 (Stahl, M. L. and Ferrari, E. (1984) J. Bacter. 158:411–418). The aprE promoter and signal peptide region was then cloned out of a pJH101 plasmid (Ferrari, F. A. et al. (1983) J. Bacter. 154:1513–1515) as a HindIII-PstI fragment and subqloned into the pUC18-derived plasmid JM102 (Ferrari, E. and Hoch, J. A. (1989) Bacillus, ed. C. R. Harwood, Plenum Pub., pp. 57–72). Addition of the Pstl-Sstl fragment from *B. licheniformis* alpha-amylase gave pA4BL (FIG. 5) having the resulting aprE signal peptide-amylase junction as shown in FIG. 6.

Transformation Into *B. subtilis* pA4BL is a plasmid able to replicate in *E. coli* and integrate into the *B. subtilis* chromosome. Plasmids containing different variants were transformed into *B. subtilis* (Anagnostopoulos, C. and Spizizen, J. (1961) J. Bacter. 81:741–746) and integrated into the chromosome at the aprE locus by a Campbell-type mechanism (Young, M. (1984) J. Gen. Microbiol. 130:1613–1621). The *Bacillus subtilis* strain BG2473 was a derivative of I168 which had been deleted for amylase (ΔamyE) and two proteases (Δapr, Δnpr) (Stahl, M. L. and Ferrari, E., J. Bacter. 158:411–418 and U.S. Pat. No. 5,264,366, incorporated herein by reference). After transformation the sacU32(Hy) (Henner, D. J. et al. (1988) J. Bacter. 170:296–300) mutation was introduced by PBS-1 mediated transduction (Hoch, J. A. (1983) 154:1513–1515).

N-terminal analysis of the amylase expressed from pA4BL in *B. subtilis* showed it to be processed having four extra alanines at the N-terminus of the secreted amylase protein ("A4 form"). These extra residues had no significant, deleterious effect on the activity or thermal stability of the A4 form and in some applications may enhance performance. In subsequent experiments the correctly processed forms of the lichenifomis amylase and the variant M197T were made from a very similar construction (see FIG. 6). Specifically, the 5' end of the A4 construction was subcloned on an EcoRI-SstII fragment, from pA4BL (FIG. 5) into M13BM20 (Boehringer Mannheim) in order to obtain a coding-strand template for the mutagenic oligonucleotide below:

5'-CAT CAG CGT CCC ATT AAG ATT TGC AGC CTG CGC AGA CAT GTT GCT-3' Seq ID No 10

This primer eliminated the codons for the extra four N-terminal alanines, correct forms being screened for by the absence of the PstI site. Subcloning the EcoRI-SstII fragment back into the pA4BL vector (FIG. 5) gave plasmid pBLapr. The M197T substitution could then be moved, on a SstII-SstI fragment, out of pA4BL (M197T) into the complementary pBLapr vector to give plasmid pBLapr (M197T). N-terminal analysis of the amylase expressed from pBLapr in *B. subtilis* showed it to be processed with the same N-terminus found in *B. licheniformis* alpha-amylase.

Example 2

Oxidative Sensitivity of Methionine Variants

*B. licheniformis* alpha-amylase, such as Spezyme® AA20 (commercially available from Genencor International, Inc.), is inactivated rapidly in the presence of hydrogen peroxide (FIG. 7). Various methionine variants were expressed in shake-flask cultures of *B. subtilis* and the crude supematants purified by ammonium sulphate cuts. The amylase was precipitated from a 20% saturated ammonium sulphate supernatant by raising the ammonium sulphate to 70% saturated, and then resuspended. The variants were then exposed to 0.88M hydrogen peroxide at pH 5.0, at 25° C. Variants at six of the methionine positions in *B. licheniformis* alpha-amylase were still subject to oxidation by peroxide while the substitution at position +197 (M197L) showed resistance to peroxide oxidation. (See FIG. 7.) However, subsequent analysis described in further detail below showed that while a variant may be susceptible to oxidation at pH 5.0, 25° C., it may exhibit altered/enhanced properties under different conditions (i.e., liquefaction).

Example 3

Construction of All Possible Variants at Position 197

All of the M197 variants (M197X) were produced in the A4 form by cassette mutagenesis, as outlined in FIG. 8:

1) Site directed mutagenesis (via primer extension in M13) was used to make M197A using the mutagenic oligonucleotide below:

```
                      M197A
5'-GAT TAT TTG GCG TAT GCC GAT ATC GAC TAT GAC CAT-3'
                           EcoRV+
                               ClaI-         Seq ID No 11
```

which also inserted an EcoRV site (codons 200–201) to replace the ClaI site (codons 201–202).

2) Then primer LAAM12 (Table II) was used to introduce another silent restriction site (BstBI) over codons 186–188.

3) The resultant M197A (BstBI+, EcoRV+) variant was then subcloned (PstI-SstI fragment) into plasmid pA4BL and the resultant plasmid digested with BstBI and EcoRV and the large vector-containing fragment isolated by electroelution from agarose gel.

4) Syntheic primers LAAM14–30 (Table II) were each annealed with the largely complementary common primer LAAM13 (Table II). The resulting cassettes encoded for all the remaining naturally occurring amino acids at position +197 and were ligated, individually, into the vector fragment prepared above.

TABLE II

| Synthetic Oligonucleotides Used for Cassette Mutagenesis to Produce M197X Variants | | |
|---|---|---|
| LAAM12 | GG GAA GTT TCG AAT GAA AAC G | Seq ID No 12 |
| LAAM13 | X197bs<br>(EcoRV) GTC GGC ATA TG CAT ATA ATC ATA GTT GCC GTT TTC ATT (BstBI) | Seq ID No 13 |
| LAAM14 | J197<br>(BstBI) CG AAT GAA AAC GGC AAC TAT GAT TAT TTG ATC TAT GCC GAC (EcoRV-) | Seq ID No 14 |
| LAAM15 | F197<br>(BstBI) CG AAT GAA AAC GGC AAC TAT GAT TAT TTG TTC TAT GCC GAC (EcoRV-) | Seq ID No 15 |
| LAAM16 | V197<br>(BstBI) CG AAT GAA AAC GGC AAC TAT GAT TAT TTG GTT TAT GCC GAC (EcoRV-) | Seq ID No 16 |
| LAAM17 | S197<br>(BstBI) CG AAT GAA AAC GGC AAC TAT GAT TAT TTG AGC TAT GCC GAC (EcoRV-) | Seq ID No 17 |
| LAAM18 | P197<br>(BstBT) CG AAT GAA AAC GGC AAC TAT GAT TAT TTG CCT TAT GCC GAC (EcoRV-) | Seq ID No 18 |
| LAAM19 | T197<br>(BstBT) CG AAT GAA AAC GGC AAC TAT GAT TAT TTG ACA TAT GCC GAC (EcoRV-) | Seq ID No 19 |
| LAAM20 | Y197<br>(BstBI) CG AAT GAA AAC GGC AAC TAT GAT TAT TTG TAC TAT GCC GAC (EcoRV-) | Seq ID No 20 |
| LAAM21 | H197<br>(BstBI) CG AAT GAA AAC GGC AAC TAT GAT TAT TTG CAC TAT GCC GAC (EcoRV-) | Seq ID No 22 |
| LAAM22 | G197<br>(BstBI) CG AAT GAA AAC GGC AAC TAT GAT TAT TTG GGC TAT GCC GAC (ECoRV-) | Seq ID No 22 |
| LAAM23 | Q197<br>(BstBI) CG AAT GAA AAC GGC AAC TAT GAT TAT TTG CAA TAT GCC GAC (EcoRV-) | Seq ID No 23 |
| LAAM24 | N197<br>(BstBI) CG AAT GAA AAC GGC AAC TAT GAT TAT TTG AAC TAT GCC GAC (EcoRV-) | Seq ID No 24 |
| LAAM25 | K197<br>(BstBI) CG AAT GAA AAC GGC AAC TAT GAT TAT TTG AAA TAT GCC GAC (EcoRV-) | Seq ID No 25 |
| LAAM26 | D197<br>(BstBI) CG AAT GAA AAC GGC AAC TAT GAT TAT TTG GAT TAT GCC GAC (EcoRV-) | Seq ID No 26 |
| LAAM27 | E197<br>(BstBI) CG AAT GAA AAC GGC AAC TAT GAT TAT TTG GAA TAT GCC GAC (EcoRV-) | Seq ID No 27 |
| LAAM28 | C197<br>(BstBI) CG AAT GAA AAC GGC AAC TAT GAT TAT TTG TGT TAT GCC GAC (EcoRV-) | Seq ID No 28 |
| LAAM29 | W197<br>(BstBI) CG AAT GAA AAC GGC AAC TAT GAT TAT TTG TGG TAT GCC GAC (EcoRV-) | Seq ID No 29 |
| LAAM30 | R197<br>(BstBI) CG AAT GAA AAC GGC AAC TAT GAT TAT TTG AGA TAT GCC GAC (EcoRV-) | Seq ID No 30 |

The cassettes were designed to destroy the EcoRV site upon ligation, thus plasmids from *E. coil* transformants were screened for loss of this unique site. In addition, the common bottom strand of the cassette contained a frame-shift and encoded a Nsil site, thus transformants derived from this strand could be eliminated by screening for the presence of the unique NsiI site and would not be expected, in any case, to lead to expression of active amylase.

Positives by restriction analysis were confirmed by sequencing and transformed in *B. subtilis* for expression in shake-flask cultures (FIG. 9). The specific activity of certain of the M197X mutants was then determined using a soluble substrate assay. The data generated using the following assay methods are presented below in Table III.

Soluble Substrate Assay: A rate assay was developed based on an end-point assay kit supplied by Megazyme (Aust.) Pty. Ltd.: Each vial of substrate (p-nitrophenyl maltoheptaoside, BPNPG7) was dissolved in 10 ml of sterile water, followed by a 1 to 4 dilution in assay buffer (50 mM maleate buffer, pH 6.7, 5 mM calcium chloride, 0.002% Tween 20). Assays were performed by adding 10 $\mu$l of amylase to 790 $\mu$l of the substrate in a cuvette at 25° C. Rates of hydrolysis were measured as the rate of change of absorbance,at 410 nm, after a delay of 75 seconds. The assay was linear up to rates of 0.4 absorption units/min.

The amylase protein concentration was measured using the standard Bio-Rad assay Bio-Rad Laboratories) based on the method of Bradford, M. (1976) Anal. Biochem. 72:248) using bovine serum albumin standards.

Starch Hydrolysis Assay: The standard method for assaying the alpha-amylase activity of Spezyme® AA20 was used. This method is described in detail in Example 1 of U.S. Ser. No. 07/785,624, incorporated herein by reference. Native starch forms a blue color with iodine but fails to do so when it is hydrolyzed into shorter dextrin molecules. The substrate is soluble Untner starch 5 gm/liter in phosphate buffer, pH 6.2 (42.5 gm/liter potassium dihydrogen phosphate, 3.6 gm/liter sodium hydroxide). The sample is added in 25 mM calcium chloride and activity is measured as the time taken to give a negative iodine test upon incubation at 30° C. Activity is recorded in liquefons per gram or ml (LU) calculated according to the formula:

$$LU/\text{ml or } LU/\text{g} = \frac{570}{V \times t} \times D.$$

Where LU=liquefon unit

V=volume of sample (5 ml)

t=dextrinization time (minutes)

D=dilution factor=dilution volume/ml or g of added enzyme.

TABLE III

| ALPHA-AMYLASE | SPECIFIC ACTIVITY (as % of AA20 value) on: Soluble Substrate | Starch |
|---|---|---|
| Spezyme ® AA20 | 100 | 100 |
| A4 form | 105 | 115 |

TABLE III-continued

| ALPHA-AMYLASE | SPECIFIC ACTIVITY (as % of AA20 value) on: Soluble Substrate | Starch |
|---|---|---|
| M15L (A4 form) | 93 | 94 |
| M15L | 85 | 103 |
| M197T (A4 form) | 75 | 83 |
| M197T | 62 | 81 |
| M197A (A4 form) | 88 | 89 |
| M197C | 85 | 85 |
| M197L (A4 form) | 51 | 17 |

Example 4

Characterization of Variant M15L

Variant M15L made as per the prior examples did not show increased amylase activity (Table III) and was still inactivated by hydrogen peroxide (FIG. 7). It did, however, show significantly increased performance in jet-liquefaction of starch especially at low pH as shown in Table IV below.

Starch liquefaction was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve.

Starch slurry was obtained from a corn wet miller and used within two days. The starch was diluted to the desired solids level with deionized water and the pH of the starch was adjusted with 2% NaOH or saturated $Na_2CO_3$. Typical liquefaction conditions were:

| | |
|---|---|
| Starch | 32%–35% solids |
| Calcium | 40–50 ppm (30 ppm added) |
| pH | 5.0–6.0 |
| Alpha-amylase | 12–14 LU/g starch dry basis |

Starch was introduced into the jet at about 350 ml/min. The jet temperature was held at 105°–107° C. Samples of starch were transferred from the jet cooker to a 95° C. second stage liquefaction and held for 90 minutes.

The degree of starch liquefaction was measured immediately after the second stage liquefaction by determining the dextrose equivalence (DE) of the sample and by testing for the presence of raw starch, both according to the methods described in the *Standard Analytical Methods of the Member Companies of the Corn Refiners Association. Inc.*, sixth edition. Starch, when treated generally under the conditions given above and at pH 6.0, will yield a liquefied starch with a DE of about 10 and with no raw starch. Results of starch liquefaction tests using mutants of the present invention are provided in Table IV.

TABLE IV

Performance of Variants M15L (A4 form) and M15L in Starch Liquefaction

| | pH | DE after 90 Mins. |
|---|---|---|
| Spezyme ® AA20 | 5.9 | 9.9 |
| M15L (A4 form) | 5.9 | 10.4 |
| Spezyme ® AA20 | 5.2 | 1.2 |
| M15L (A4 form) | 5.2 | 2.2 |
| Spezyme ® AA20 | 5.9 | 9.3* |
| M15L | 5.9 | 11.3* |
| Spezyme ® AA20 | 5.5 | 3.25** |
| M15L | 5.5 | 6.7** |
| Spezyme ® AA20 | 5.2 | 0.7** |
| M15L | 5.2 | 3.65** |

*average of three experiments
**average of two experiments

Example 5

Construction of M15X Variants

Following generally the processes described in Example 3 above, all variants at M15 (M15X) were produced in native *B. licheniformis* by cassette mutagenesis, as outlined in FIG. 12:

1) Site directed mutagenesis (via primer extension in M13) was used to introduce unique restriction sites flanking the M15 codon to facilitate insertion of a mutagenesis cassette. Specifically, a BstB1 site at codons 11–13 and a Msc1 site at codons 18–20 were introduced using the two oligonucleotides shown below.

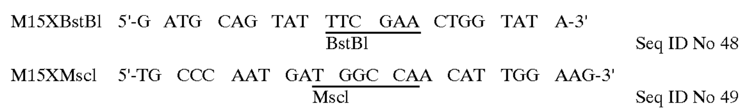

2) The vector for M15X cassette mutagenesis was then constructed by subcloning the Sfi1–SstII fragment from the mutagenized amylase (BstB1+, Msc1+) into plasmid pBLapr. The resulting plasmid was then digested with BstB1 and Msc1 and the large vector fragment isolated by electroelution from a polyacrylamide gel.
3) Mutagenesis cassettes were created as with the M197X variants. Synthetic oligomers, each encoding a substitution at codon 15, were annealed to a common bottom primer. Upon proper ligation of the cassette to the vector, the Msc1 is destroyed allowing for screening of positive transformants by loss of this site. The bottom primer contains an unique SnaB1 site allowing for the transformants derived from the bottom strand to be eliminated by screening for the SnaB1 site. This primer also contains a frameshift which would also eliminate amylase expression for the mutants derived from the common bottom strand.

The synthetic cassettes are listed in Table V and the general cassette mutagenesis strategy is illustrated in FIG. 12.

TABLE V

| Synthetic Oligonucleotides Used for Cassette Mutagenesis to Produce M15X Variants | | | |
|---|---|---|---|
| M15A | (BstB1) | C GAA TGG TAT GCT CCC AAT GAC GG (Msc1) | Seq ID No 50 |
| M15R | (BstB1) | C GAA TGG TAT CGC CCC AAT GAC GG (Msc1) | Seq ID No 51 |
| M15N | (BstB1) | C GAA TGG TAT AAT CCC AAT GAC GG (Msc1) | Seq ID No 52 |
| M15D | (BstB1) | C GAA TGG TAT GAT CCC AAT GAC GG (Msc1) | Seq ID No 53 |
| M15H | (BstB1) | C GAA TGG TAT CAC CCC AAT GAC GG (Msc1) | Seq ID No 54 |
| M15K | (BstB1) | C GAA TGG TAT AAA CCC AAT GAC GG (Msc1) | Seq ID No 55 |
| M15P | (BstB1) | C GAA TGG TAT CCG CCC AAT GAC GG (Msc1) | Seq ID No 56 |
| M15S | (BstB1) | C GAA TGG TAT TCT CCC AAT GAC GG (Msc1) | Seq ID No 57 |
| M1ST | (BstB1) | C GAA TGG TAC ACT CCC AAT GAC GG (Msc1) | Seq ID No 58 |
| M15V | (BstB1) | C GAA TGG TAT GTT CCC AAT GAC GG (Msc1) | Seq ID No 59 |
| M15C | (BstB1) | C GAA TGG TAT TGT CCC AAT GAC GG (Msc1) | Seq ID No 60 |
| M15Q | (BstB1) | C GAA TGG TAT CAA CCC AAT GAC GG (Msc1) | Seq ID No 61 |
| M15E | (BstB1) | C GAA TGG TAT GAA CCC AAT GAC GG (Msc1) | Seq ID No 62 |
| M15G | (BstB1) | C GAA TGG TAT GGT CCC AAT GAC GG (Msc1) | Seq ID No 63 |
| M15I | (BstB1) | C GAA TGG TAT ATT CCC AAT GAC GG (Msc1) | Seq ID No 64 |
| M15F | (BstB1) | C GAA TGG TAT TTT CCC AAT GAC GG (Msc1) | Seq ID No 65 |
| M15W | (BstB1) | C GAA TGG TAC TGG CCC AAT GAC GG (Msc1) | Seq ID No 66 |
| M15Y | (BstB1) | C GAA TGG TAT TAT CCC AAT GAC GG (Msc1) | Seq ID No 67 |
| M15X (bottom strand) | (Msc1) | CC GTC ATT GGG ACT ACG TAC CAT T (BstB1) | Seq ID No 68 |

Underline indicates codon changes at amino acid position 15.
Conservative substitutions were made in some cases to prevent introduction of new restriction sites.

Example 6

Bench Liquefaction with M15X Variants

Eleven alpha-amylase variants with substitutions for M15 made as per Example 5 were assayed for activity, as compared to Spezyme® AA20 (commercially available from Genencor International, Inc.) in liquefaction at pH 5.5 using a bench liquefaction system. The bench scale liquefaction system consisted of a stainless steel coil (0.25 inch diameter, approximately 350 ml volume) equipped with a 7 inch long static mixing element approximately 12 inches from the anterior end and a 30 psi back pressure valve at the posterior end. The coil, except for each end, was immersed in a glycerol-water bath equipped with thermostatically controlled heating elements that maintained the bath at 105°–106° C.

Starch slurry containing enzyme, maintained in suspension by stirring, was introduced into the reaction coil by a piston driven metering pump at about 70 ml/min. The starch was recovered from the end of the coil and was transferred to the secondary hold (95° C. for 90 minutes). Immediately after the secondary hold, the DE of the liquefied starch was determined, as described in Example 4. The results are shown in FIG. 16.

Example 7

Characterization of M197X Variants

As can be seen in FIG. 9, there was a wide range of amylase activity (measured in the soluble substrate assay) expressed by the M197X (A4 form) variants. The amylases were partially purified from the supematants by precipitation with two volumes of ethanol and resuspension. They were then screened for thermal stability (FIG. 10) by heating at 95° C. for 5 minutes in 10 mM acetate buffer pH 5.0, in the presence of 5 mM calcium chloride; the A4 wild-type retained 28% of its activity after incubation. For M197W and M197P we were unable to recover active protein from the supernatants. Upon sequencing, the M197H variant was found to contain a second mutation, N190K. M197L was examined in a separate experiment and was one of the lowest thermally stable variants. There appears to be a broad correlation between expression of amylase activity and thermal stability. The licheniforrnis amylase is restricted in what residues it can accommodate at position 197 in terms of retaining or enhancing thermal stability: cysteine and threonine are preferred for maximal thermal stability under these conditions whereas alanine and isoleucine are of intermediate stability. However, other substitutions at position +197 result in lowered thermal stability which may be useful for other applications. Additionally, different substitutions at +197 may have other beneficial properties, such as altered pH performance profile or altered oxidative stability. For example, the M197C variant was found to inactivate readily by air oxidation but had enhanced thermal stability. Conversely, compared to the M197L variant, both M197T and M197A retained not only high thermal stability (FIG. 10), but also high activity (Table III), while maintaining resistance to inactivation by peroxide at pH 5 to pH 10 (FIG. 7).

Example 8

Stability and Performance in Detergent Formulation

The stability of the M197T (A4 form), M197T and M197A (A4 form) was measured in automatic dish care detergent (ADD) matrices. 2 ppm Savinase™ (a protease, commercially available from Novo Industries, of the type commonly used in ADD) were added to two commercially available bleach-containing ADD's: Cascade™ (Procter and Gamble, Ltd.) and Sunlight™ (Unilever) and the time course of inactivation of the amylase variants and Termamyl™ (a thermally stable alpha-amylase available from Novo Nordisk, A/S) followed at 65° C. The concentration of ADD product used in both cases was equivalent to 'pre-soak' conditions: 14 gm product per liter of water (7 grams per gallon hardness). As can be seen (FIGS. 11a and 11b), both forms of the M197T variant were much more stable than Termamyl™ and M197A (A4 form), which were inactivated before the first assay could be performed. This stability benefit was seen in the presence or absence of starch as determined by the following protocol. Amylases were added to 5ml of ADD and Savinase™, prewarmed in a test tube and, after vortexing, activities were assayed as a function of time, using the soluble substrate assay. The "+starch" tube had spaghetti starch baked onto the sides (140° C. 60 mins.). The results are shown in FIGS. 11a and 11b.

Example 9

Characterization of M15X Variants

All M15X variants were propagated in *Bacillus subtilis* and the expression level monitored as shown in FIG. 13. The amylase was isolated and partially purified by a 20–70% ammonium sulfate cut. The specific activity of these variants on the soluble substrate was determined as per Example 3 (FIG. 14). Many of the M15X amylases have specific activities greater than that of Spezyme® AA20. A benchtop heat stability assay was performed on the variants by heating the amylase at 90° C. for 5 min. in 50 mM acetate buffer pH 5 in the presence of 5 mM $CaCl_2$ (FIG. 15). Most of the variants performed as well as Spezyme® AA20 in this assay. Those variants that exhibited reasonable stability in this assay (reasonable stability defined as those that retained at least about 60% of Spezyme® AA20's heat stability) were tested for specific activity on starch and for liquefaction performance at pH 5.5. The most interesting of those mutants are shown in FIG. 16. M15D, N and T, along with L, outperformed Spezyme® AA20 in liquefaction at pH 5.5 and have increased specific activities in both the soluble substrate and starch hydrolysis assays.

Generally, we have found that by substituting for the methionine at position 15, we can provide variants with increased low pH-liquefaction performance and/or increased specific activity.

Example 10

Tryptophan Sensitivity to Oxidation

Chloramine-T (sodium N-chloro-p-toluenesulfonimide) is a selective oxidant, which oxidizes methionine to methionine sulfoxide at neutral or alkaline pH. At acidic pH, chloramine-T will modify both methionine and tryptophan (Schechter, Y., Burstein, Y. and Patchomik, A. (1975) Biochemistry 14 (20) 4497–4503). FIG. 17 shows the inactivation of *B. licheniformis* alpha-amylase with chloramine-T at pH 8.0 (AA20=0.65 mg/ml, M197A=1.7 mg/ml, M197L=1.7 mg/ml). The data shows that by changing the methionine at position 197 to leucine or alanine, the inactivation of alpha-amylase can be prevented. Conversely, as shown in FIG. 18, at pH 4.0 inactivation of the M197A and M197L proceeds, but require more equivalents of chloramine-T (FIG. 18; A20=0.22 mg/ml, M197A=4.3 mg/ml, M197L=0.53 mg/ml; 200 mM NaAcetate at pH 4.0). This suggests that a tryptophan residue is also implicated in the chloramine-T mediated inactivation event. Furthermore, tryptic mapping and subsequent amino acid sequencing indicated that the tryptophan at position 138 was oxidized by chloramine-T (data not shown). To prove this, site-directed mutants were made at tryptophan 138 as provided below:

Preparation of Alpha-Amylase Double Mutants W138 and M197

Certain variants of W138 (F, Y and A) were made as double mutants, with M197T (made as per the disclosure of Example 3). The double mutants were made following the methods described in Examples 1 and 3. Generally,single negative strands of DNA were prepared from an M13MP18 clone of the 1.72kb coding sequence (PstI-SstI) of the *B. licheniformis* alpha-amylase M197T mutant. Site-directed mutagenesis was done using the primers listed below, essentially by the method of Zoller, M. et al. (1983) except T4 gene 32 protein and T4 polymerase were substituted for klenow. The primers all contained unique sites, as well as the desired mutation, in order to identify those clones with the appropriate mutation.

Tryptophan 138 to Phenylalanine

```
133  134  135  136  137  138  139  140  141  142  143
CAC  CTA  ATT  AAA  GCT  TTC  ACA  CAT  TTT  CAT  TTT          Seq ID No 42
                Hind III
```

Tryptophan 138 to Tyrosine

```
133  134  135  136  137  138  139  140  141  142  143
CAC  CTA  ATT  AAA  GCT  TAC  ACA  CAT  TTT  CAT  TTT          Seq ID No 43
                Hind III
```

Tyrptophan 138 to Alanine- This primer also engineers unique sites upsteam and downstream of the 138 position.

```
  127  128  129  130  131  132  133  134  135  136  137  138  139  140  141  142
C CGC  GTA  ATT  TCC  GGA  GAA  CAC  CTA  ATT  AAA  GCC  GCA  ACA  CAT  TTT  CAT
                   BspE I

143  144  145  146  147
TTT  CCC  GGG  CGC  GGC  AG                                     Seq ID No 44
      Xma I
```

Mutants were identified by restriction analysis and W138F and W138Y confirmed by DNA sequencing. The W138A sequence revealed a nucleotide deletion between the unique BspE I and Xma I sites, however, the rest of the gene sequenced correctly. The 1.37 kb Sstll/Ssti fragment containing both W138X and M197T mutations was moved from M13MP18 into the expression vector pBLapr resulting in pBLapr (W138F, M197T) and pBLapr (W138Y, M197T). The fragment containing unique BspE I and Xma I sites was cloned into pBLapr (BspEI, XmaI, M197T) since it is useful for cloning cassettes containing other amino acid substitutions at position 138.

Single Mutations at Amino Acid Position138

Following the general methods described in the prior examples, certain single variants of W138 (F, Y, L, H and C) were made.

The 1.24 kb Asp718-SstI fragment containing the M197T mutation in plasmid pBLapr (WI138X, M197T) of Example 7 was replaced by the wild-type fragment with methionine at 197, resulting in pBLapr (W138F), pBLapr (W138Y) and pSLapr (BspE I, Xma I).

The mutants W138L, W138H and W138C were made by ligating synthetic cassettes into the pBLapr (BspE I, Xma I) vector using the following primers:

| | |
|---|---|
| Tryptophan 138 to Leucine | |
| CC GGA GAA CAC CTA ATT AAA GCC CTA ACA CAT TTT CAT TTT C | Seq ID No 45 |
| Tryptophan 138 to Histidine | |
| CC GGA GAA CAC CTA ATT AAA GCC CAC ACA CAT TTT CAT TTT C | Seq ID No 46 |
| Tryptophan 138 to Cysteine | |
| CC GGA GAA CAC CTA ATT AAA GCC TGC ACA CAT TTT CAT TTT C | Seq ID No 47 |

Reaction of the double mutants M197T/W138F and M197T/W138Y with chloramine-T was compared with wild-type (AA20=0.75 mg/ml, M197T/W138F=0.64 mg/ml, M197T/W138Y=0.60 mg/ml; 50 mM NaAcetate at pH 5.0). The results shown in FIG. 19 show that mutagenesis of tryptophan 138 has caused the variant to be more resistant to chloramine-T.

What is claimed is:

1. A method of liquefying a granular starch slurry from either a wet or dry milling process at a pH of from about 4 to less than about 6 comprising:

adding to the slurry an effective amount of a mutant alpha-amylase derived from Bacillus, the alpha-amylase mutant comprising a substitution of threonine, leucine, asparagine or aspartic acid for a methionine residue corresponding to M15 in *Bacillus licheniformis* alpha-amylase; optionally adding an effective amount of an antioxidant to the slurry; and reacting the slurry for an appropriate time and at an appropriate temperature to liquefy the starch.

2. A method of liquefying a granular starch slurry from either a wet or dry milling process at a pH of from about 4 to less than about 6 comprising:

adding to the slurry an effective amount of a mutant alpha-amylase derived from Bacillus, the alpha-amylase mutant comprising a substitution of leucine or alanine for a methionine residue corresponding to M197 in *Bacillus licheniformis* alpha-amylase; optionally adding an effective amount of an antioxidant to the slurry; and reacting the slurry for an appropriate time and at an appropriate temperature to liquefy the starch.

* * * * *

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GATCAAAACA TAAAAAACCG GCCTTGGCCC CGCCGGTTTT TTATTATTTT TGAGCT 56

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TGGGACGCTG GCGCAGTACT TTGAATGGT 29

( 2 ) INFORMATION FOR SEQ ID NO:3:

( i ) SEQUENCE CHARACTERISTICS:
( A ) LENGTH: 34 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:3:

TGATGCAGTA CTTTGAATGG TACCTGCCCA ATGA 34

( 2 ) INFORMATION FOR SEQ ID NO:4:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GATTATTTGT TGTATGCCGA TATCGACTAT GACCAT 36

( 2 ) INFORMATION FOR SEQ ID NO:5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

CGGGGAAGGA GGCCTTTACG GTAGCT 26

( 2 ) INFORMATION FOR SEQ ID NO:6:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GCGGCTATGA CTTAAGGAAA TTGC 24

( 2 ) INFORMATION FOR SEQ ID NO:7:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

CTACGGGGAT GCATACGGGA CGA 23

( 2 ) INFORMATION FOR SEQ ID NO:8:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CTACGGGGAT TACTACGGGA CCAAGGGAGA CTCCC 35

(2) INFORMATION FOR SEQ ID NO:9:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

CCGGTGGGGC CAAGCGGGCC TATGTTGGCC GGCAAA 36

(2) INFORMATION FOR SEQ ID NO:10:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

CATCAGCGTC CCATTAAGAT TTGCAGCCTG CGCAGACATG TTGCT 45

(2) INFORMATION FOR SEQ ID NO:11:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GATTATTTGG CGTATGCCGA TATCGACTAT GACCAT 36

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GGGAAGTTTC GAATGAAAAC G 21

(2) INFORMATION FOR SEQ ID NO:13:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GTCGGCATAT GCATATAATC ATAGTTGCCG TTTTCATT 38

(2) INFORMATION FOR SEQ ID NO:14:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

CGAATGAAAA CGGCAACTAT GATTATTTGA TCTATGCCGA C 41

( 2 ) INFORMATION FOR SEQ ID NO:15:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

CGAATGAAAA CGGCAACTAT GATTATTTGT TCTATGCCGA C 41

( 2 ) INFORMATION FOR SEQ ID NO:16:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

CGAATGAAAA CGGCAACTAT GATTATTTGG TTTATGCCGA C 41

( 2 ) INFORMATION FOR SEQ ID NO:17:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CGAATGAAAA CGGCAACTAT GATTATTTGA GCTATGCCGA C 41

( 2 ) INFORMATION FOR SEQ ID NO:18:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CGAATGAAAA CGGCAACTAT GATTATTTGC CTTATGCCGA C 41

( 2 ) INFORMATION FOR SEQ ID NO:19:

( i ) SEQUENCE CHARACTERISTICS:
( A ) LENGTH: 41 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:19:

CGAATGAAAA CGGCAACTAT GATTATTTGA CATATGCCGA C 41

( 2 ) INFORMATION FOR SEQ ID NO:20:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CGAATGAAAA CGGCAACTAT GATTATTTGT ACTATGCCGA C 41

( 2 ) INFORMATION FOR SEQ ID NO:21:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:21:

CGAATGAAAA CGGCAACTAT GATTATTTGC ACTATGCCGA C 41

( 2 ) INFORMATION FOR SEQ ID NO:22:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:22:

CGAATGAAAA CGGCAACTAT GATTATTTGG GCTATGCCGA C 41

( 2 ) INFORMATION FOR SEQ ID NO:23:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:23:

CGAATGAAAA CGGCAACTAT GATTATTTGC AATATGCCGA C 41

( 2 ) INFORMATION FOR SEQ ID NO:24:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:24:

CGAATGAAAA CGGCAACTAT GATTATTTGA ACTATGCCGA C 41

( 2 ) INFORMATION FOR SEQ ID NO:25:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:25:

GCAATGAAAA CGGCAACTAT GATTATTTGA AATATGCCGA C 41

( 2 ) INFORMATION FOR SEQ ID NO:26:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

CGAATGAAAA CGGCAACTAT GATTATTTGG ATTATGCCGA C 41

( 2 ) INFORMATION FOR SEQ ID NO:27:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

CGAATGAAAA CGGCAACTAT GATTATTTGG AATATGCCGA C 41

( 2 ) INFORMATION FOR SEQ ID NO:28:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

CGAATGAAAA CGGCAACTAT GATTATTTGT GTATTGCCGA C 41

( 2 ) INFORMATION FOR SEQ ID NO:29:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:29:

CGAATGAAAA CGGCAACTAT GATTATTTGT GGTATGCCGA C 41

( 2 ) INFORMATION FOR SEQ ID NO:30:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:30:

CGAATGAAAA CGGCAACTAT GATTATTTGA GATATGCCGA C 41

( 2 ) INFORMATION FOR SEQ ID NO:31:

( i ) SEQUENCE CHARACTERISTICS:
( A ) LENGTH: 1968 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:31:

AGCTTGAAGA AGTGAAGAAG CAGAGAGGCT ATTGAATAAA TGAGTAGAAA GCGCCATATC 60

GGCGCTTTTC TTTTGGAAGA AAATATAGGG AAAATGGTAC TTGTTAAAAA TTCGGAATAT 120

TTATACAACA TCATATGTTT CACATTGAAA GGGGAGGAGA ATCATGAAAC AACAAAAACG 180

GCTTTACGCC CGATTGCTGA CGCTGTTATT TGCGCTCATC TTCTTGCTGC CTCATTCTGC 240

AGCAGCGGCG GCAAATCTTA ATGGGACGCT GATGCAGTAT TTTGAATGGT ACATGCCCAA 300

TGACGGCCAA CATTGGAAGC GTTTGCAAAA CGACTCGGCA TATTTGGCTG AACACGGTAT 360

TACTGCCGTC TGGATTCCCC CGGCATATAA GGGAACGAGC CAAGCGGATG TGGGCTACGG 420

TGCTTACGAC CTTTATGATT TAGGGGAGTT TCATCAAAAA GGGACGGTTC GGACAAAGTA 480

CGGCACAAAA GGAGAGCTGC AATCTGCGAT CAAAAGTCTT CATTCCCGCG ACATTAACGT 540

TTACGGGGAT GTGGTCATCA ACCACAAAGG CGGCGCTGAT GCGACCGAAG ATGTAACCGC 600

GGTTGAAGTC GATCCCGCTG ACCGCAACCG CGTAATTTCA GGAGAACACC TAATTAAAGC 660

CTGGACACAT TTTCATTTTC CGGGGCGCGG CAGCACATAC AGCGATTTTA AATGGCATTG 720

GTACCATTTT GACGGAACCG ATTGGGACGA GTCCCGAAAG CTGAACCGCA TCTATAAGTT 780

TCAAGGAAAG GCTTGGGATT GGGAAGTTTC CAATGAAAAC GGCAACTATG ATTATTTGAT 840

GTATGCCGAC ATCGATTATG ACCATCCTGA TGTCGCAGCA GAAATTAAGA GATGGGGCAC 900

TTGGTATGCC AATGAACTGC AATTGGACGG TTTCCGTCTT GATGCTGTCA AACACATTAA 960

ATTTTCTTTT TTGCGGGATT GGGTTAATCA TGTCAGGGAA AAAACGGGGA AGGAAATGTT 1020

TACGGTAGCT GAATATTGGC AGAATGACTT GGGCGCGCTG GAAAACTATT TGAACAAAAC 1080

AAATTTTAAT CATTCAGTGT TTGACGTGCC GCTTCATTAT CAGTTCCATG CTGCATCGAC 1140

ACAGGGAGGC GGCTATGATA TGAGGAAATT GCTGAACGGT ACGGTCGTTT CCAAGCATCC 1200

GTTGAAATCG GTTACATTTG TCGATAACCA TGATACACAG CCGGGGCAAT CGCTTGAGTC 1260

GACTGTCCAA ACATGGTTTA AGCCGCTTGC TTACGCTTTT ATTCTCACAA GGGAATCTGG 1320

ATACCCTCAG GTTTTCTACG GGGATATGTA CGGGACGAAA GGAGACTCCC AGCGCGAAAT 1380

TCCTGCCTTG AAACACAAAA TTGAACCGAT CTTAAAAGCG AGAAAACAGT ATGCGTACGG 1440

AGCACAGCAT GATTATTTCG ACCACCATGA CATTGTCGGC TGGACAAGGG AAGGCGACAG 1500

CTCGGTTGCA AATTCAGGTT TGGCGGCATT AATAACAGAC GGACCCGGTG GGCAAAGCG 1560

AATGTATGTC GGCCGGCAAA ACGCCGGTGA GACATGGCAT GACATTACCG GAAACCGTTC 1620

-continued

```
GGAGCCGGTT GTCATCAATT CGGAAGGCTG GGGAGAGTTT CACGTAAACG GCGGGTCGGT   1680
TTCAATTTAT GTTCAAAGAT AGAAGAGCAG AGAGGACGGA TTTCCTGAAG GAAATCCGTT   1740
TTTTTATTTT GCCCGTCTTA TAAATTTCTT TGATTACATT TTATAATTAA TTTTAACAAA   1800
GTGTCATCAG CCCTCAGGAA GGACTTGCTG ACAGTTTGAA TCGCATAGGT AAGGCGGGGA   1860
TGAAATGGCA ACGTTATCTG ATGTAGCAAA GAAAGCAAAT GTGTCGAAAA TGACGGTATC   1920
GCGGGTGATC AATCATCCTG AGACTGTGAC GGATGAATTG AAAAAGCT                1968
```

(2) INFORMATION FOR SEQ ID NO:32:

(i) SEQUENCE CHARACTERISTICS:
(A) LENGTH: 483 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:32:

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285
```

His Tyr Gln Phe His Ala Ala Ser Thr Gln Gly Gly Gly Tyr Asp Met
290 295 300

Arg Lys Leu Leu Asn Gly Thr Val Val Ser Lys His Pro Leu Lys Ser
305 310 315 320

Val Thr Phe Val Asp Asn His Asp Thr Gln Pro Gly Gln Ser Leu Glu
325 330 335

Ser Thr Val Gln Thr Trp Phe Lys Pro Leu Ala Tyr Ala Phe Ile Leu
340 345 350

Thr Arg Glu Ser Gly Tyr Pro Gln Val Phe Tyr Gly Asp Met Tyr Gly
355 360 365

Thr Lys Gly Asp Ser Gln Arg Glu Ile Pro Ala Leu Lys His Lys Ile
370 375 380

Glu Pro Ile Leu Lys Ala Arg Lys Gln Tyr Ala Tyr Gly Ala Gln His
385 390 395 400

Asp Tyr Phe Asp His His Asp Ile Val Gly Trp Thr Arg Glu Gly Asp
405 410 415

Ser Ser Val Ala Asn Ser Gly Leu Ala Ala Leu Ile Thr Asp Gly Pro
420 425 430

Gly Gly Ala Lys Arg Met Tyr Val Gly Arg Gln Asn Ala Gly Glu Thr
435 440 445

Trp His Asp Ile Thr Gly Asn Arg Ser Glu Pro Val Val Ile Asn Ser
450 455 460

Glu Gly Trp Gly Glu Phe His Val Asn Gly Gly Ser Val Ser Ile Tyr
465 470 475 480

Val Gln Arg ( 2 ) INFORMATION FOR SEQ ID NO:33:

( i ) SEQUENCE CHARACTERISTICS:
( A ) LENGTH: 511 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:33:

Met Lys Gln Gln Lys Arg Leu Tyr Ala Arg Leu Leu Thr Leu Leu Phe
1 5 10 15

Ala Leu Ile Phe Leu Leu Pro His Ser Ala Ala Ala Ala Ala Asn Leu
20 25 30

Asn Gly Thr Leu Met Gln Tyr Phe Glu Trp Tyr Met Pro Asn Asp Gly
35 40 45

His Trp Lys Arg Leu Gln Asn Asp Ser Ala Tyr Leu Ala Glu His Gly
50 55 60

Ile Thr Ala Val Trp Ile Pro Pro Ala Tyr Lys Gly Thr Ser Gln Ala
65 70 75 80

Asp Val Gly Tyr Gly Ala Tyr Asp Leu Tyr Asp Leu Gly Glu Phe His
85 90 95

Gln Lys Gly Thr Val Arg Thr Lys Tyr Gly Thr Lys Gly Glu Leu Gln
100 105 110

Ser Ala Ile Lys Ser Leu His Ser Arg Asp Ile Asn Val Tyr Gly Asp
115 120 125

Val Val Ile Asn His Lys Gly Gly Ala Asp Ala Thr Glu Asp Val Thr
130 135 140

Ala Val Glu Val Asp Pro Ala Asp Arg Asn Arg Val Ile Ser Gly Glu
145 150 155 160

His Leu Ile Lys Ala Trp Thr His Phe His Phe Pro Gly Arg Gly Ser
165 170 175

Thr Tyr Ser Asp Phe Lys Trp His Trp Tyr His Phe Asp Gly Thr Asp
180 185 190

Trp Asp Glu Ser Arg Lys Leu Asn Arg Ile Tyr Lys Phe Gln Gly Lys
195 200 205

Ala Trp Asp Trp Glu Val Ser Asn Glu Asn Gly Asn Tyr Asp Tyr Leu
210 215 220

Met Tyr Ala Asp Ile Asp Tyr Asp His Pro Asp Val Ala Ala Glu Ile
225 230 235 240

Lys Arg Trp Gly Thr Trp Tyr Ala Asn Glu Leu Gln Leu Asp Gly Phe
245 250 255

Arg Leu Asp Ala Val Lys His Ile Lys Phe Ser Phe Leu Arg Asp Trp
260 265 270

Val Asn His Val Arg Glu Lys Thr Gly Lys Glu Met Phe Thr Val Ala
275 280 285

Glu Tyr Trp Gln Asn Asp Leu Gly Ala Leu Glu Asn Tyr Leu Asn Lys
290 295 300

Thr Asn Phe Asn His Ser Val Phe Asp Val Pro Leu His Tyr Gln Phe
305 310 315 320

His Ala Ala Ser Thr Gln Gly Gly Gly Tyr Asp Met Arg Lys Leu Leu
325 330 335

Asn Gly Thr Val Val Ser Lys His Pro Leu Lys Ser Val Thr Phe Val
340 345 350

Asp Asn His Asp Thr Gln Pro Gly Gln Ser Leu Glu Ser Thr Val Gln
355 360 365

Thr Trp Phe Lys Pro Leu Ala Tyr Ala Phe Ile Leu Thr Arg Glu Ser
370 375 380

Gly Tyr Pro Gln Val Phe Tyr Gly Asp Met Tyr Gly Thr Lys Gly Asp
385 390 395 400

Ser Gln Arg Glu Ile Pro Ala Leu Lys His Lys Ile Glu Pro Ile Leu
405 410 415

Lys Ala Arg Lys Gln Tyr Ala Tyr Gly Ala Gln His Asp Tyr Phe Asp
420 425 430

His His Asp Ile Val Gly Trp Thr Arg Glu Gly Asp Ser Ser Val Ala
435 440 445

Asn Ser Gly Leu Ala Ala Leu Ile Thr Asp Gly Pro Gly Gly Ala Lys
450 455 460

Arg Met Tyr Val Gly Arg Gln Asn Ala Gly Glu Thr Trp His Asp Ile
465 470 475 480

Thr Gly Asn Arg Ser Glu Pro Val Val Ile Asn Ser Glu Gly Trp Gly
485 490 495

Glu Phe His Val Asn Gly Gly Ser Val Ser Ile Tyr Val Gln Arg
500 505 510

( 2 ) INFORMATION FOR SEQ ID NO:34:

( i ) SEQUENCE CHARACTERISTICS:
( A ) LENGTH: 520 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:34:

-continued

Met Arg Gly Arg Gly Asn Met Ile Gln Lys Arg Lys Arg Thr Val Ser
1 5 10 15

Phe Arg Leu Val Leu Met Cys Thr Leu Leu Phe Val Ser Leu Pro Ile
20 25 30

Thr Lys Thr Ser Ala Val Asn Gly Thr Leu Met Gln Tyr Phe Glu Trp
35 40 45

Tyr Thr Pro Asn Asp Gly Gln His Trp Lys Arg Leu Gln Asn Asp Ala
50 55 60

Glu His Leu Ser Asp Ile Gly Ile Thr Ala Val Trp Ile Pro Pro Ala
65 70 75 80

Tyr Lys Gly Leu Ser Gln Ser Asp Asn Gly Tyr Gly Pro Tyr Asp Leu
85 90 95

Tyr Asp Leu Gly Glu Phe Gln Gln Lys Gly Thr Val Arg Thr Lys Tyr
100 105 110

Gly Thr Lys Ser Glu Leu Gln Asp Ala Ile Gly Ser Leu His Ser Arg
115 120 125

Asn Val Gln Val Tyr Gly Asp Val Val Leu Asn His Lys Ala Gly Ala
130 135 140

Asp Ala Thr Glu Asp Val Thr Ala Val Glu Val Asn Pro Ala Asn Arg
145 150 155 160

Asn Gln Glu Thr Ser Glu Glu Tyr Gln Ile Lys Ala Trp Thr Asp Phe
165 170 175

Arg Phe Pro Gly Arg Gly Asn Thr Tyr Ser Asp Phe Lys Trp His Trp
180 185 190

Tyr His Phe Asp Gly Ala Asp Trp Asp Glu Ser Arg Lys Ile Ser Arg
195 200 205

Ile Phe Lys Phe Arg Gly Glu Gly Lys Ala Trp Asp Trp Glu Val Ser
210 215 220

Ser Glu Asn Gly Asn Tyr Asp Tyr Leu Met Tyr Ala Asp Val Asp Tyr
225 230 235 240

Asp His Pro Asp Val Val Ala Glu Thr Lys Lys Trp Gly Ile Trp Tyr
245 250 255

Ala Asn Glu Leu Ser Leu Asp Gly Phe Arg Ile Asp Ala Ala Lys His
260 265 270

Ile Lys Phe Ser Phe Leu Arg Asp Trp Val Gln Ala Val Arg Gln Ala
275 280 285

Thr Gly Lys Glu Met Phe Thr Val Ala Glu Tyr Trp Gln Asn Asn Ala
290 295 300

Gly Lys Leu Glu Asn Tyr Leu Asn Lys Thr Ser Phe Asn Gln Ser Val
305 310 315 320

Phe Asp Val Pro Leu His Phe Asn Leu Gln Ala Ala Ser Ser Gln Gly
325 330 335

Gly Gly Tyr Asp Met Arg Arg Leu Leu Asp Gly Thr Val Val Ser Arg
340 345 350

His Pro Glu Lys Ala Val Thr Phe Val Glu Asn His Asp Thr Gln Pro
355 360 365

Gly Gln Ser Leu Glu Ser Thr Val Gln Thr Trp Phe Lys Pro Leu Ala
370 375 380

Tyr Ala Phe Ile Leu Thr Arg Glu Ser Gly Tyr Pro Gln Val Phe Tyr
385 390 395 400

Gly Asp Met Tyr Gly Thr Lys Gly Thr Ser Pro Lys Glu Ile Pro Ser
405 410 415

Leu Lys Asp Asn Ile Glu Pro Ile Leu Lys Ala Arg Lys Glu Tyr Ala
420 425 430

```
Tyr Gly Pro Gln His Asp Tyr Ile Asp His Pro Asp Val Ile Gly Trp
        435                 440                 445

Thr Arg Glu Gly Asp Ser Ser Ala Ala Lys Ser Gly Leu Ala Ala Leu
    450                 455                 460

Ile Thr Asp Gly Pro Gly Gly Ser Lys Arg Met Tyr Ala Gly Leu Lys
465                 470                 475                 480

Asn Ala Gly Glu Thr Trp Tyr Asp Ile Thr Gly Asn Arg Ser Asp Thr
                485                 490                 495

Val Lys Ile Gly Ser Asp Gly Trp Gly Glu Phe His Val Asn Asp Gly
            500                 505                 510

Ser Val Ser Ile Tyr Val Gln Lys
        515                 520
```

( 2 ) INFORMATION FOR SEQ ID NO:35:

( i ) SEQUENCE CHARACTERISTICS:
( A ) LENGTH: 548 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:35:

```
Val Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Arg His Ala
            20                  25                  30

Lys Ala Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Ser Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
        115                 120                 125

Gly Met Gln Val Tyr Ala Asp Val Val Phe Asp His Lys Gly Gly Ala
    130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Arg Gly Ile Gly Lys Ala Trp Asp Trp Glu Val Asp
    210                 215                 220

Thr Glu Asn Gly Asn Tyr Asp Tyr Leu Met Tyr Ala Asp Leu Asp Met
225                 230                 235                 240

Asp His Pro Glu Val Val Thr Glu Leu Lys Asn Trp Gly Lys Trp Tyr
                245                 250                 255
```

-continued

Val Asn Thr Thr Asn Ile Asp Gly Phe Arg Leu Asp Gly Leu Lys His
260 265 270

Ile Lys Phe Ser Phe Phe Pro Asp Trp Leu Ser Tyr Val Arg Ser Gln
275 280 285

Thr Gly Lys Pro Leu Phe Thr Val Gly Glu Tyr Trp Ser Tyr Asp Ile
290 295 300

Asn Lys Leu His Asn Tyr Ile Thr Lys Thr Asn Gly Thr Met Ser Leu
305 310 315 320

Phe Asp Ala Pro Leu His Asn Lys Phe Tyr Thr Ala Ser Lys Ser Gly
325 330 335

Gly Ala Phe Asp Met Arg Thr Leu Met Thr Asn Thr Leu Met Lys Asp
340 345 350

Gln Pro Thr Leu Ala Val Thr Phe Val Asp Asn His Asp Thr Asn Pro
355 360 365

Ala Lys Arg Cys Ser His Gly Arg Pro Trp Phe Lys Pro Leu Ala Tyr
370 375 380

Ala Phe Ile Leu Thr Arg Gln Glu Gly Tyr Pro Cys Val Phe Tyr Gly
385 390 395 400

Asp Tyr Tyr Gly Ile Pro Gln Tyr Asn Ile Pro Ser Leu Lys Ser Lys
405 410 415

Ile Asp Pro Leu Leu Ile Ala Arg Arg Asp Tyr Ala Tyr Gly Thr Gln
420 425 430

His Asp Tyr Leu Asp His Ser Asp Ile Ile Gly Trp Thr Arg Glu Gly
435 440 445

Val Thr Glu Lys Pro Gly Ser Gly Leu Ala Ala Leu Ile Thr Asp Gly
450 455 460

Ala Gly Arg Ser Lys Trp Met Tyr Val Gly Lys Gln His Ala Gly Lys
465 470 475 480

Val Phe Tyr Asp Leu Thr Gly Asn Arg Ser Asp Thr Val Thr Ile Asn
485 490 495

Ser Asp Gly Trp Gly Glu Phe Lys Val Asn Gly Gly Ser Val Ser Val
500 505 510

Trp Val Pro Arg Lys Thr Thr Val Ser Thr Ile Ala Arg Pro Ile Thr
515 520 525

Thr Arg Pro Trp Thr Gly Glu Phe Val Arg Trp His Glu Pro Arg Leu
530 535 540

Val Ala Trp Pro
545

( 2 ) INFORMATION FOR SEQ ID NO:36:

( i ) SEQUENCE CHARACTERISTICS:
( A ) LENGTH: 483 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

Ala Asn Leu Asn Gly Thr Leu Met Gln Tyr Phe Glu Trp Tyr Met Pro
1 5 10 15

Asn Asp Gly Gln His Trp Lys Arg Leu Gln Asn Asp Ser Ala Tyr Leu
20 25 30

Ala Glu His Gly Ile Thr Ala Val Trp Ile Pro Pro Ala Tyr Lys Gly
35 40 45

-continued

Thr Ser Gln Ala Asp Val Gly Tyr Gly Ala Tyr Asp Leu Tyr Asp Leu
50 55 60

Gly Glu Phe His Gln Lys Gly Thr Val Arg Thr Lys Tyr Gly Thr Lys
65 70 75 80

Gly Glu Leu Gln Ser Ala Ile Lys Ser Leu His Ser Arg Asp Ile Asn
85 90 95

Val Tyr Gly Asp Val Val Ile Asn His Lys Gly Gly Ala Asp Ala Thr
100 105 110

Glu Asp Val Thr Ala Val Glu Val Asp Pro Ala Asp Arg Asn Arg Val
115 120 125

Ile Ser Gly Glu His Leu Ile Lys Ala Trp Thr His Phe His Phe Pro
130 135 140

Gly Arg Gly Ser Thr Tyr Ser Asp Phe Lys Trp His Trp Tyr His Phe
145 150 155 160

Asp Gly Thr Asp Trp Asp Glu Ser Arg Lys Leu Asn Arg Ile Tyr Lys
165 170 175

Phe Gln Gly Lys Ala Trp Asp Trp Glu Val Ser Asn Glu Asn Gly Asn
180 185 190

Tyr Asp Tyr Leu Thr Tyr Ala Asp Ile Asp Tyr Asp His Pro Asp Val
195 200 205

Ala Ala Glu Ile Lys Arg Trp Gly Thr Trp Tyr Ala Asn Glu Leu Gln
210 215 220

Leu Asp Gly Phe Arg Leu Asp Ala Val Lys His Ile Lys Phe Ser Phe
225 230 235 240

Leu Arg Asp Trp Val Asn His Val Arg Glu Lys Thr Gly Lys Glu Met
245 250 255

Phe Thr Val Ala Glu Tyr Trp Gln Asn Asp Leu Gly Ala Leu Glu Asn
260 265 270

Tyr Leu Asn Lys Thr Asn Phe Asn His Ser Val Phe Asp Val Pro Leu
275 280 285

His Tyr Gln Phe His Ala Ala Ser Thr Gln Gly Gly Gly Tyr Asp Met
290 295 300

Arg Lys Leu Leu Asn Gly Thr Val Val Ser Lys His Pro Leu Lys Ser
305 310 315 320

Val Thr Phe Val Asp Asn His Asp Thr Gln Pro Gly Gln Ser Leu Glu
325 330 335

Ser Thr Val Gln Thr Trp Phe Lys Pro Leu Ala Tyr Ala Phe Ile Leu
340 345 350

Thr Arg Glu Ser Gly Tyr Pro Gln Val Phe Tyr Gly Asp Met Tyr Gly
355 360 365

Thr Lys Gly Asp Ser Gln Arg Glu Ile Pro Ala Leu Lys His Lys Ile
370 375 380

Glu Pro Ile Leu Lys Ala Arg Lys Gln Tyr Ala Tyr Gly Ala Gln His
385 390 395 400

Asp Tyr Phe Asp His His Asp Ile Val Gly Trp Thr Arg Glu Gly Asp
405 410 415

Ser Ser Val Ala Asn Ser Gly Leu Ala Ala Leu Ile Thr Asp Gly Pro
420 425 430

Gly Gly Ala Lys Arg Met Tyr Val Gly Arg Gln Asn Ala Gly Glu Thr
435 440 445

Trp His Asp Ile Thr Gly Asn Arg Ser Glu Pro Val Val Ile Asn Ser
450 455 460

Glu Gly Trp Gly Glu Phe His Val Asn Gly Gly Ser Val Ser Ile Tyr
465 470 475 480

Val Gln Arg ( 2 ) INFORMATION FOR SEQ ID NO:37:

( i ) SEQUENCE CHARACTERISTICS:
( A ) LENGTH: 487 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:37:

Ala Ala Ala Ala Ala Asn Leu Asn Gly Thr Leu Met Gln Tyr Phe Glu
1 5 10 15

Trp Tyr Met Pro Asn Asp Gly Gln His Trp Lys Arg Leu Gln Asn Asp
20 25 30

Ser Ala Tyr Leu Ala Glu His Gly Ile Thr Ala Val Trp Ile Pro Pro
35 40 45

Ala Tyr Lys Gly Thr Ser Gln Ala Asp Val Gly Tyr Gly Ala Tyr Asp
50 55 60

Leu Tyr Asp Leu Gly Glu Phe His Gln Lys Gly Thr Val Arg Thr Lys
65 70 75 80

Tyr Gly Thr Lys Gly Glu Leu Gln Ser Ala Ile Lys Ser Leu His Ser
85 90 95

Arg Asp Ile Asn Val Tyr Gly Asp Val Val Ile Asn His Lys Gly Gly
100 105 110

Ala Asp Ala Thr Glu Asp Val Thr Ala Val Glu Val Asp Pro Ala Asp
115 120 125

Arg Asn Arg Val Ile Ser Gly Glu His Leu Ile Lys Ala Trp Thr His
130 135 140

Phe His Phe Pro Gly Arg Gly Ser Thr Tyr Ser Asp Phe Lys Trp His
145 150 155 160

Trp Tyr His Phe Asp Gly Thr Asp Trp Asp Glu Ser Arg Lys Leu Asn
165 170 175

Arg Ile Tyr Lys Phe Gln Gly Lys Ala Trp Asp Trp Glu Val Ser Asn
180 185 190

Glu Asn Gly Asn Tyr Asp Tyr Leu Met Tyr Ala Asp Ile Asp Tyr Asp
195 200 205

His Pro Asp Val Ala Ala Glu Ile Lys Arg Trp Gly Thr Trp Tyr Ala
210 215 220

Asn Glu Leu Gln Leu Asp Gly Phe Arg Leu Asp Ala Val Lys His Ile
225 230 235 240

Lys Phe Ser Phe Leu Arg Asp Trp Val Asn His Val Arg Glu Lys Thr
245 250 255

Gly Lys Glu Met Phe Thr Val Ala Glu Tyr Trp Gln Asn Asp Leu Gly
260 265 270

Ala Leu Glu Asn Tyr Leu Asn Lys Thr Asn Phe Asn His Ser Val Phe
275 280 285

Asp Val Pro Leu His Tyr Gln Phe His Ala Ala Ser Thr Gln Gly Gly
290 295 300

Gly Tyr Asp Met Arg Lys Leu Leu Asn Gly Thr Val Val Ser Lys His
305 310 315 320

Pro Leu Lys Ser Val Thr Phe Val Asp Asn His Asp Thr Gln Pro Gly
325 330 335

-continued

```
Gln Ser Leu Glu Ser Thr Val Gln Thr Trp Phe Lys Pro Leu Ala Tyr
            340                 345                 350

Ala Phe Ile Leu Thr Arg Glu Ser Gly Tyr Pro Gln Val Phe Tyr Gly
        355                 360                 365

Asp Met Tyr Gly Thr Lys Gly Asp Ser Gln Arg Glu Ile Pro Ala Leu
    370                 375                 380

Lys His Lys Ile Glu Pro Ile Leu Lys Ala Arg Lys Gln Tyr Ala Tyr
385                 390                 395                 400

Gly Ala Gln His Asp Tyr Phe Asp His His Asp Ile Val Gly Trp Thr
                405                 410                 415

Arg Glu Gly Asp Ser Ser Val Ala Asn Ser Gly Leu Ala Ala Leu Ile
            420                 425                 430

Thr Asp Gly Pro Gly Gly Ala Lys Arg Met Tyr Val Gly Arg Gln Asn
        435                 440                 445

Ala Gly Glu Thr Trp His Asp Ile Thr Gly Asn Arg Ser Glu Pro Val
    450                 455                 460

Val Ile Asn Ser Glu Gly Trp Gly Glu Phe His Val Asn Gly Gly Ser
465                 470                 475                 480

Val Ser Ile Tyr Val Gln Arg
                485
```

( 2 ) INFORMATION FOR SEQ ID NO:38:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:38:

```
Met Lys Gln Gln Lys Arg Leu Thr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30
```

( 2 ) INFORMATION FOR SEQ ID NO:39:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:39:

```
Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser
```

( 2 ) INFORMATION FOR SEQ ID NO:40:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:40:

Met Arg Ser Lys Thr Leu Trp Ile Ser Leu Leu Phe Ala Leu Thr Leu
1 5 10 15

Ile Phe Thr Met Ala Phe Ser Asn Met Ser Ala Gln Ala Ala Ala Ala
20 25 30

Ala Ala Asn
35

( 2 ) INFORMATION FOR SEQ ID NO:41:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:41:

Met Arg Ser Lys Thr Leu Trp Ile Ser Leu Leu Phe Ala Leu Thr Leu
1 5 10 15

Ile Phe Thr Met Ala Phe Ser Asn Met Ser Ala Gln Ala Ala Asn Leu
20 25 30

( 2 ) INFORMATION FOR SEQ ID NO:42:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

CACCTAATTA AAGCTTTCAC ACATTTTCAT TTT 33

( 2 ) INFORMATION FOR SEQ ID NO:43:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:43:

CACCTAATTA AAGCTTACAC ACATTTTCAT TTT 33

( 2 ) INFORMATION FOR SEQ ID NO:44:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:44:

CCGCGTAATT TCCGGAGAAC ACCTAATTAA AGCCGCAACA CATTTTCATT TTCCCGGGCG 60

CGGCAG 66

( 2 ) INFORMATION FOR SEQ ID NO:45:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:45:

CCGGAGAACA CCTAATTAAA GCCCTAACAC ATTTTCATTT TC 42

( 2 ) INFORMATION FOR SEQ ID NO:46:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:46:

CCGGAGAACA CCTAATTAAA GCCCACACAC ATTTTCATTT TC 42

( 2 ) INFORMATION FOR SEQ ID NO:47:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:47:

CCGGAGAACA CCTAATTAAA GCCTGCACAC ATTTTCATTT TC 42

( 2 ) INFORMATION FOR SEQ ID NO:48:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:48:

GATGCAGTAT TTCGAACTGG TATA 24

( 2 ) INFORMATION FOR SEQ ID NO:49:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:49:

TGCCCAATGA TGGCCAACAT TGGAAG 26

( 2 ) INFORMATION FOR SEQ ID NO:50:

( i ) SEQUENCE CHARACTERISTICS:
( A ) LENGTH: 24 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:50:

C G A A T G G T A T G C T C C C A A T G A C G G 2 4

( 2 ) INFORMATION FOR SEQ ID NO:51:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:51:

C G A A T G G T A T C G C C C C A A T G A C G G 2 4

( 2 ) INFORMATION FOR SEQ ID NO:52:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:52:

C G A A T G G T A T A A T C C C A A T G A C G G 2 4

( 2 ) INFORMATION FOR SEQ ID NO:53:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:53:

C G A A T G G T A T G A T C C C A A T G A C G G 2 4

( 2 ) INFORMATION FOR SEQ ID NO:54:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:54:

C G A A T G G T A T C A C C C C A A T G A C G G 2 4

( 2 ) INFORMATION FOR SEQ ID NO:55:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:55:

CGAATGGTAT AAACCCAATG ACGG 24

(2) INFORMATION FOR SEQ ID NO:56:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:56:

CGAATGGTAT CCGCCCAATG ACGG 24

(2) INFORMATION FOR SEQ ID NO:57:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:57:

CGAATGGTAT TCTCCCAATG ACGG 24

(2) INFORMATION FOR SEQ ID NO:58:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:58:

CGAATGGTAC ACTCCCAATG ACGG 24

(2) INFORMATION FOR SEQ ID NO:59:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:59:

CGAATGGTAT GTTCCCAATG ACGG 24

(2) INFORMATION FOR SEQ ID NO:60:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:60:

CGAATGGTAT TGTCCCAATG ACGG 24

(2) INFORMATION FOR SEQ ID NO:61:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:61:

CGAATGGTAT CAACCCAATG ACGG 24

( 2 ) INFORMATION FOR SEQ ID NO:62:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:62:

CGAATGGTAT GAACCCAATG ACGG 24

( 2 ) INFORMATION FOR SEQ ID NO:63:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:63:

CGAATGGTAT GGTCCCAATG ACGG 24

( 2 ) INFORMATION FOR SEQ ID NO:64:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:64:

CGAATGGTAT ATTCCCAATG ACGG 24

( 2 ) INFORMATION FOR SEQ ID NO:65:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:65:

CGAATGGTAT TTTCCCAATG ACGG 24

( 2 ) INFORMATION FOR SEQ ID NO:66:

( i ) SEQUENCE CHARACTERISTICS:
( A ) LENGTH: 24 base pairs
( B ) TYPE: nucleic acid
( C ) STRANDEDNESS: single ( D ) TOPOLOGY: linear ( i i ) MOLECULE TYPE: DNA (genomic)

( x i ) SEQUENCE DESCRIPTION: SEQ ID NO:66:

CGAATGGTAC TGGCCCAATG ACGG 24

( 2 ) INFORMATION FOR SEQ ID NO:67:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:67:

CGAATGGTAT TATCCCAATG ACGG 24

( 2 ) INFORMATION FOR SEQ ID NO:68:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:68:

CCGTCATTGG GACTACGTAC CATT 24